US010072079B2

United States Patent
Ehninger

(10) Patent No.: US 10,072,079 B2
(45) Date of Patent: Sep. 11, 2018

(54) ISOLATED HUMAN MESENCHYMAL STEM CELL EXPRESSING A BISPECIFIC ANTIBODY THAT BINDS CD33 AND CD3

(71) Applicant: GEMoaB Monoclonals GmbH, Dresden (DE)

(72) Inventor: Armin Ehninger, Dresden (DE)

(73) Assignee: GEMoaB Monoclonals GmbH, Dresden (DE)

( * ) Notice: Subject to any disclaimer, the term of this patent is extended or adjusted under 35 U.S.C. 154(b) by 132 days.

(21) Appl. No.: 14/959,784

(22) Filed: Dec. 4, 2015

(65) Prior Publication Data

US 2016/0159909 A1    Jun. 9, 2016

Related U.S. Application Data

(60) Provisional application No. 62/088,578, filed on Dec. 6, 2014.

(30) Foreign Application Priority Data

May 5, 2015 (EP) ..................................... 15166347

(51) Int. Cl.

| | |
|---|---|
| *C12N 5/00* | (2006.01) |
| *C12N 5/02* | (2006.01) |
| *C12N 15/00* | (2006.01) |
| *C07K 16/28* | (2006.01) |
| *A61K 35/28* | (2015.01) |
| *C12N 5/0775* | (2010.01) |

(52) U.S. Cl.
CPC .......... *C07K 16/2809* (2013.01); *A61K 35/28* (2013.01); *C07K 16/2803* (2013.01); *C12N 5/0663* (2013.01); *C07K 2317/31* (2013.01); *C07K 2317/76* (2013.01); *C12N 2510/00* (2013.01); *C12N 2510/02* (2013.01)

(58) Field of Classification Search
USPC ............................... 435/325, 455; 424/93.21
See application file for complete search history.

(56) References Cited

U.S. PATENT DOCUMENTS

2006/0269526 A1    11/2006   Galipeau et al.

OTHER PUBLICATIONS

Compte (Cancer Gene Therapy, 2007, vol. 14, p. 380-388).*
Compte (Stem Cells, 2009, vol. 27, p. 753-760).*
Arndt (Leukemia, 2014, vol. 28, No. 1, p. 59-69.*
Frequencies of Cell Types in human PBL, 2017.*
Compte, M., et al., "Tumor Immunotherapy Using Gene-Modified Human Mesenchymal Stem Cells Loaded into Synthetic Extracellular Matrix Scaffolds", Stem Cells, vol. 27, pp. 753-760 (2009).
Compte, M., et al., "Factory Neovessels: Engineered Human Blood Vessels Secreting Therapeutic Proteins as a New Drug Delivery System", Gene Therapy, vol. 17, pp. 745-751 (2010).
Klyushnenkova, E., et al. "T Cell Responses to Allogeneic Human Mesenchymal Stem Cells: Immunogenicity, Tolerance, and Suppression", Journal of Biomedical Science, vol. 12, pp. 47-57 (2005).
Romieu-Mourez, R., et al., "Mesenchymal Stromal Cells as Effective Tumor Antigen-Presenting Cells in Cancer Therapeutics", Stem Cell Therapeutics for Cancer, First Edition, Chapter 10, pp. 127-143 (2013).
Ling, V., et al., "Differential Expression of Inducible Costimulator-Ligand Splice Variants: Lymphoid Regulation of Mouse GL50-B and Human GL50 Molecules", The Journal of Immunology, vol. 166(12), pp. 7300-7308 (2001).
Chen, L., et al., "Molecular Mechanisms of T Cell Co-Stimulation and Co-Inhibition", Nature Reviews, Immunology, vol. 13(4), pp. 227-242 (2013).
Weidle, U., et al., "The Intriguing Options of Multispecific Antibody Formats for Treatment of Cancer", Cancer Genomics & Proteomics, vol. 10(1), pp. 1-18 (2013).
European Search Report for EP15166347 dated Jul. 23, 2015.
Arndt, C. et al., "Costimulation improves the killing capability of T cells redirected to tumor cells expressing low levels of CD33: description of a novel modular targeting system", Leukemia, vol. 28, No. 1, Jan. 1, 2014, pp. 59-69.
Communication Pursuant to Article 94(3) EPC dated May 9, 2017.

* cited by examiner

Primary Examiner — Michael C Wilson
(74) Attorney, Agent, or Firm — Heslin Rothenberg Farley and Mesiti, PC

(57) ABSTRACT

The invention concerns pluri- or multipotent stem cells (SCs), e.g. human pluri- or multipotent stem cells (hSCs) engineered to express a multispecific antibody and which further express, on their surface, a human immune cell co-stimulatory ligand or an active fragment thereof.

5 Claims, 14 Drawing Sheets

Specification includes a Sequence Listing.

ISOLATED HUMAN MESENCHYMAL STEM CELL EXPRESSING A BISPECIFIC ANTIBODY THAT BINDS CD33 AND CD3

CROSS-REFERENCE TO RELATED APPLICATIONS

This application claims priority benefit of European Patent Application No. EP 15 166 347.3, filed May 5, 2015, and U.S. Provisional Patent Application Ser. No. 62/088,578, filed Dec. 6, 2014, the disclosures of which are hereby incorporated by reference herein in their entirety.

FIELD OF THE INVENTION

The invention concerns pluri- or multipotent stem cells (SCs), e.g. human pluri- or multipotent stem cells (hSCs) engineered to express a multispecific antibody and which further expresses, on its surface, a human immune cell co-stimulatory ligand or an active fragment thereof.

BACKGROUND OF THE INVENTION

The use of recombinant bispecific antibodies (bsabs) for retargeting effector T lymphocytes towards cancer cells is recently emerging as a promising immunotherapeutic tool for the treatment of hematologic malignancies and other cancers. The high efficacy of this class of molecules in redirecting specifically CD8+ and CD4+ T cells to any chosen tumor associated antigen (TAA) on the surface of tumor cells by cross-linking their activating CD3 receptor has been reported in many preclinical and clinical studies. Nonetheless, due to their low molecular mass, bsabs have a short half-life in vivo and consequently have to be continuously administered to patients over prolonged time spans of several weeks to achieve clinical responses (Schlereth et al. 2005, Stork et al. 2008, Bargou et al. 2008, Handgretinger et al. 2011). External medical pump devices as currently used in clinical trials can be a potential source of infection. Thus there is a need to improve the route of application for this highly effective class of drugs for treating disorders such as cancer. An alternative to continuous infusion through external medical pump devices are gene-modified cells, which continuously produce and secrete bsabs for their life-time in the body of the patient.

Kasuya, et al. (Kasuya et al., Int. J. Mol Med, 25, 2010, 209-215) report the production of a bispecific anti-HER2 and anti-CD16 antibody by embryonic fibroblasts that have been transplanted into immunodeficient mice.

In addition Compte and colleagues, (Compte, et al., Stem Cells, 2099, 27, 753-760) disclose a tumor immunotherapy by use of gene-modified human mesenchymal stem cells (hMSC) for producing a bispecific anti-CEA and anti-CD3 antibody.

Furthermore Frank, et al. (Frank, et al., PloSone, 2009, 4, e831) used neural stem cells (NSC) as a novel platform for tumor specific delivery of therapeutic antibodies.

Although several advances in the use of genetically modified cells for producing therapeutic antibodies have been made, there are still limitations that have to be overcome.

The present invention is directed to overcoming these and other deficiencies in the art.

SUMMARY OF THE INVENTION

It is an object of the present invention to provide genetically modified cells engineered to produce multispecific antibodies and an improved method for in situ delivery of therapeutic antibodies by these genetically modified cells.

The objective is solved by using pluri- or multipotent stem cells according to the present invention.

In one aspect, provided herein are pluri- or multipotent stem cells engineered to express a multispecific antibody, which further express on their surface a human immune cell co-stimulatory ligand or an active fragment thereof.

The term pluri- or multipotent stem cell (SC) refers to any stem cell other than an embryonic stem cell or stem cell derived from embryo or fetus. The term pluri- or multipotent stem cell (SC) excludes cells from embryo or fetus and includes cells that can be found in children, as well as in adults or that is generated by genetic manipulation of a somatic cell.

The term pluri- or multipotent stem cell (SC) refers to stem cells comprising mesenchymal stem cells (MSC), neural stem cells (NSC), endothelial progenitor cells (EPC), hematopoietic stem cells (HSC) and induced pluripotent stem cell (iPSC). Preferably the stem cells are human stem cells.

In a preferred embodiment the pluri- or multipotent stem cells are human mesenchymal stem cells (hMSC).

In certain embodiments, the human immune cell co-stimulatory ligand or an active fragment thereof, which can be recombinantly expressed on the cell surface of SCs, provided herein is selected from a group of CD28 ligands CD80 (B7-1) and CD86 (B7-2), CD137 ligand (CD137L, 4-1BBL), Ox40L ligand OX40L (CD252), CD27 ligand CD70 (CD27L), Inducible T-cell Costimulator (ICOS) ligand ICOSL (CD275), lymphocyte function-associated antigen (LFA) 1 ligand intercellular adhesion molecule (ICAM)-1 (CD54), -2 (CD102), and -3 (CD50), and ligands of the signaling lymphocytic activation molecule (SLAM) family e.g. 2B4 (CD244) ligand SLAMF2 (CD48).

In certain embodiments the pluri- or multipotent stem cells are engineered to express multispecific antibodies, comprising at least a target cell specific binding domain and at least an immune cell specific binding domain.

The two specific domains (target cell and immune cell) are preferably expressed as a fusion protein.

The target cell specific binding domain is preferably specific for a tumor associated antigen or an antigen of a pathogen, parasite or parasitoid.

More preferred, the target cell specific binding domain is specific for an antigen selected from surface, cytoplasmic or nuclear antigens like the La/SSB antigen, CD19, CD20, CD22, CD33, CD38, CD56, CD157, CD123, CCR5, STEAP1, prostate stem cell antigen PSCA, prostate specific membrane antigen PSMA, members of the epidermal growth factor receptor family, preferably EGFR (ErbB-1), HER2/neu (ErbB-2), Her3 (ErbB-3) and Her4 (ErbB-4) and mutants thereof, members of the ephrin receptor family, preferably EphA1-10 or EphB1-6, embryonic antigens, preferably carcinoembryonic antigen CEA, fetal acethylcholine receptor, CEACAM-6, CEACAM-7.

Next most preferred, the target cell specific binding domain is specific for an antigen selected from members of the Rho family of GTPases, members of the high mobility group proteins, bladder tumor antigen (BTA), CA125, CD2, CD4, CD8, CD10, CD23, CD30, CD44, CD52, CD99, CD135, CD274, Carboanhydrase IX, Endosialin, fibroblast-activating protease-alpha (FAP-alpha), FBP, gpA33, gp100, c-Met (hepatocyte growth factor receptor), MCSP and TIM-3, members of the vascular endothelia growth factor family (VEGFR 1-3), epithelia cell adhesion molecule EpCAM, alphafetoprotein AFP, members of the mucin protein family, preferably MUC1 or MUC16, follicle stimulating hormone receptor (FSHR), the human high molecular weight-melanoma-associated antigen (HMW-MAA), folate binding protein FBP, a-Folate receptor, ligands of the NKG2D receptor, members of the epithelia glycoprotein family, preferably EGP-2, EGP-4 or EGP-40, members of the insulin-like growth factor receptor family, preferably IGF-1R, diasialogangliosides, preferably GD2 or GD3, members of the carbonic anhydrase family, preferably CAIX, members of the carbohydrate antigen family, preferably Ley, including mutants of the named proteins and protein families and viral envelope proteins, preferably gp120, gp41 or EBOV GP.

Alternatively preferred, the target cell binding domain is composed of the alpha and beta or the gamma and delta chains of a T cell receptor (TCR) or fragments thereof. Such TCR-derived binding moieties recognize and bind to peptides presented by human leukocyte antigen class (HLA) I and II protein complexes. Preferred examples are, but are not limited to, TCRs specific for viral peptides, peptides derived from proteins like EGFR family, survivin, sry-like high motility group box (SOX) protein family, melanoma-associated antigens, preferably autoimmunogenic cancer/testis antigen NY-ESO-1, members of the melanoma antigen family A MAGEA, the preferentially expressed antigen in melanoma PRAIVIE, and leukemia-associated antigens, preferably wilms tumor gene 1 WT1. The target cell binding moiety could also comprise ligands to proteins and protein complexes, further on referred as receptors. Such ligands may bind to, but are not limited to, cytokine receptors, preferably IL-13 receptor, ligands of the NKG2D receptor, ligands to the EGFR family members, or auto-reactive TCRs.

For the generation of permanent SCs expressing multispecific antibodies, e.g. bispecific antibodies, cDNA encoding a recombinant antibody, preferably multispecific antibody, such as bispecific antibody construct can, for example, be cloned into a viral vector (e.g., self-inactivating retroviral vector), such as a retroviral vector or lentiviral vector, preferably p6NST50 to generate a transfer vector. In this viral vector, the expression of a recombinant antibody (e.g., multispecific antibody, such as bispecific antibody) can be driven by a suitable promoter, such as a viral promoter, e.g., spleen focus forming virus (SFFV)-derived internal promoter. In certain embodiments, an enhanced green fluorescence protein (EGFP)-Zeocin fusion protein can be co-expressed by an internal ribosomal entry site (IRES). Lentiviral particles pseudotyped with an envelope protein, e.g., the Vesicular Stomatitis Virus envelope 120 (VSV-G), can be generated by transient transfection of a packaging cell, e.g., HEK293T cells, and virus supernatant are harvested and used to stably transduce SCs, such as SCP-1 cells.

For ectopic expression of a co-stimulary ligand, e.g., the co-stimulatory 4-1BB ligand (CD137L), on the surface of SCs, such as SCP-1 cells, a viral vector, such as a retroviral vector or a lentiviral vector, can be used which harbors an appropriate mammalian promoter, such as an internal minimal human elongation factor 1 alpha promoter.

In a particular aspect, SCs can be co-transfected with two or more expression vectors (e.g., viral vectors) encoding polypeptides that associate (e.g., covalently or noncovalently) to form antigen binding domains (e.g., antigen-binding domains comprising a VH and a VL) of an antibody (e.g., multispecific antibody, such as bispecific antibody) expressed by SCs.

In certain embodiments, at least 1 pg, 5 pg, 10 pg, 50 pg, 75 pg, 100 pg, 250 pg of antibody are produced per cell over a period of 48 hours. In other embodiments, at most 1 pg, 5 pg, 10 pg, 50 pg, 75 pg, 100 pg, 250 pg of antibody are produced per cell over a period of 48 hours. In certain embodiments, 5-10, 5-50, 10-50, 25-75, or 8-70 pg of antibody are produced per cell over a period of 48 hours.

In specific aspects, provided herein are multispecific antibodies, such as bispecific antibodies, which are recombinantly expressed by SCs, wherein the multispecific antibodies comprising at least a target cell specific binding domain and at least an immune cell specific binding domain.

The two specific domains (target cell and immune cell) are preferably expressed as a fusion protein.

The target cell specific binding domain is preferably specific for a tumor associated antigen or an antigen of a pathogen, parasite or parasitoid.

The tumor antigen can be associated, but is not restricted to, hematopoietic and lymphoid malignancies like leukemia (e.g. acute lymphoblastic leukemia, acute myelogenous leukemia or chronic lymphocytic or myelogenous leukemia), lymphoma (e.g. non-Hodgkin and Hodgkin lymphomas) or myeloma. It can be also associated with carcinoma (e.g. breast, prostate, lung, pancreas or colon carcinoma), sarcoma (e.g. osteosarcoma, Ewing's sarcoma), or blastoma (e.g. neuroblastoma, glioblastoma multifome).

In certain aspects, a bispecific antibody provided herein is a single chain bispecific antibody. In a particular embodiment, a bispecific antibody provided herein, such as a single chain bispecific antibody, is humanized (e.g., humanized bispecific antibody targeting CD33 and CD3).

As used herein, the terms "variable region" or "variable domain" refer to a portion of an antibody, generally, a portion of an antibody light or heavy chain, typically about the amino-terminal 110 to 120 amino acids in a mature heavy chain and about the amino-terminal 90 to 100 amino acids in a mature light chain. Variable regions comprise complementarity determining regions (CDRs) flanked by framework regions (FRs). Generally, the spatial orientation of CDRs and FRs are as follows, in an N-terminal to C-terminal direction: FR1-CDR1-FR2-CDR2-FR3-CDR3-FR4. Without wishing to be bound by any particular mechanism or theory, it is believed that the CDRs of the light and heavy chains are primarily responsible for the interaction of the antibody with antigen and for the specificity of the antibody for an epitope.

In a specific embodiment, numbering of amino acid positions of antibodies described herein is according to the EU Index, as in Kabat et al. (1991) *Sequences of Proteins of Immunological Interest*, Fifth Edition, U.S. Department of Health and Human Services, NIH Publication No. 91-3242. In certain embodiments, the variable region is a human variable region. In certain embodiments, the variable region comprises murine (e.g., mouse or rat) CDRs and human framework regions (FRs). In particular embodiments, the variable region is a primate (e.g., human or non-human primate) variable region. In certain embodiments, the variable region comprises murine (e.g., mouse or rat) CDRs and primate (e.g., human or non-human primate) framework regions (FRs). As a non-limiting example, a variable region described herein is obtained from assembling two or more fragments of human sequences into a composite human sequence.

In certain aspects, the CDRs of an antibody can be determined according to (i) the Kabat numbering system (Kabat et al. (1971) *Ann. NY Acad. Sci.* 190:382-391 and, Kabat et al. (1991) *Sequences of Proteins of Immunological Interest*, Fifth Edition, U.S. Department of Health and Human Services, NIH Publication No. 91-3242); or (ii) the Chothia numbering scheme, which will be referred to herein as the "Chothia CDRs" (see, e.g., Chothia and Lesk, 1987, J. Mol. Biol., 196:901-917; Al-Lazikani et al., 1997, J. Mol. Biol., 273:927-948; Chothia et al., 1992, J. Mol. Biol., 227:799-817; Tramontano A et al., 1990, J. Mol. Biol. 215(1):175-82; and U.S. Pat. No. 7,709,226); or (iii) the ImMunoGeneTics (IMGT) numbering system, for example, as described in Lefranc, M.-P., 1999, The Immunologist, 7:132-136 and Lefranc, M.-P. et al., 1999, Nucleic Acids Res., 27:209-212 ("IMGT CDRs"); or (iv) MacCallum et al., 1996, J. Mol. Biol., 262:732-745. See also, e.g., Martin, A., "Protein Sequence and Structure Analysis of Antibody Variable Domains," in *Antibody Engineering*, Kontermann and Dübel, eds., Chapter 31, pp. 422-439, Springer-Verlag, Berlin (2001).

In a specific aspect, provided herein are SCs expressing multispecific antibodies, e.g., bispecific antibodies, such as single chain bispecific antibodies, comprising a VL and a VH targeting a tumor associated antigen or an antigen of a pathogen, parasite or parasitoid. In specific aspects, multispecific antibodies, such as bispecific antibodies, e.g., single chain bispecific antibodies, described herein comprise one or more linkers (e.g., one, two, three, four, or five, or more linkers).

In a certain embodiment, such a linker described herein comprises repetitions, for example, at least one, two, three, four or five repetitions, of glycine-serine, e.g., $G_4S$ linkers.

In a specific embodiment, provided herein are SCs expressing a multispecific antibody, e.g., bispecific antibody, such as a single chain bispecific antibody, which specifically binds to a tumor associated antigen or an antigen of a pathogen, parasite or parasitoid comprising a heavy chain variable region (VH) and a light chain variable region (VL).

In specific embodiments, multispecific antibodies, such as, bispecific antibodies, e.g., single chain bispecific antibodies, described herein comprises at the N-terminus a signal peptide, e.g., an Ig kappa leader sequence as signal peptide, for protein secretion.

In certain embodiments, multispecific antibodies, such as, bispecific antibodies, e.g., single chain bispecific antibodies, described herein comprises at the C-terminus a tag, for example, myc-tag or and histidine (his)-tag (e.g, 6×his-tag) for protein purification and/or detection.

In certain embodiments, antibodies (e.g., multispecific antibodies, such as bispecific antibodies) described herein can be of any type (e.g., IgG, IgE, IgM, IgD, IgA or IgY), any class, (e.g., $IgG_1$, $IgG_2$, $IgG_3$, $IgG_4$, $IgA_1$ or $IgA_2$), or any subclass (e.g., $IgG_{2a}$ or $IgG_{2b}$, or a mixture thereof) of immunoglobulin molecules.

In specific embodiments, multispecific antibodies, such as, bispecific antibodies, e.g., single chain bispecific antibodies, described herein do not comprise an antibody constant region.

Methods for making multispecific (e.g, bispecific antibodies) have been described, see, for example, U.S. Pat. Nos. 7,951,917, 7,183,076, 8,227,577, 5,837,242, 5,989,830, 5,869,620, 6,132,992, and 8,586,713.

In certain embodiments, the presently disclosed methods and uses enhance the T cell response against a cancer cell. Without being bound by theory, the improved T cell response against a cancer cell is accomplished by targeting of pluri- or multipotent stem cells to the cancer cell in a patient. In certain embodiments, at least $1\times10^5$, $2\times10^5$, $3\times10^5$, $4\times10^5$, $5\times10^5$, $6\times10^5$, $7\times10^5$, $8\times10^5$, $9\times10^5$, $1\times10^6$, $2\times10^6$, $3\times10^6$, $4\times10^6$, $5\times10^6$, $6\times10^6$, $7\times10^6$, $8\times10^6$, $9\times10^6$, or at least $1\times10^7$ SCs as described herein are administered to a patient. In certain embodiments, at most $1\times10^5$, $2\times10^5$, $3\times10^5$, $4\times10^5$, $5\times10^5$, $6\times10^5$, $7\times10^5$, $8\times10^5$, $9\times10^5$, $1\times10^6$, $2\times10^6$, $3\times10^6$, $4\times10^6$, $5\times10^6$, $6\times10^6$, $7\times10^6$, $8\times10^6$, $9\times10^6$, or at least $1\times10^7$ SCs as described herein are administered to a patient. In a more specific embodiment between $5\times10^6$ and $6\times10^6$ SCs as described herein are administered to a patient.

In certain embodiments, at least 1 mg, 2 mg, 3 mg, 4 mg, 5 mg, 6 mg, 7 mg, 8 mg, 9 mg, or at least 10 mg cell mass of an SC as described herein can be transplanted into a patient. In certain embodiments, at most 1 mg, 2 mg, 3 mg, 4 mg, 5 mg, 6 mg, 7 mg, 8 mg, 9 mg, or at least 10 mg cell mass of an SC as described herein can be transplanted into a patient. In certain embodiments, about 1 mg, 2 mg, 3 mg, 4 mg, 5 mg, 5.5 mg, 6 mg, 7 mg, 8 mg, 9 mg, or at least 10 mg cell mass of an SC as described herein can be transplanted into a patient.

SCs can be used as in situ producer of anti-cancer therapeuticals. In certain embodiments, autologous gene-modified SCs as described herein can be injected intravenously into patients and, without being bound by theory, migrate to the tumor site and deliver their payload locally.

In certain embodiment, the use of SCs for in situ production of anti-cancer therapeutics (eg, multispecific or bispecific antibodies) results in continuous delivery of the anti-cancer therapeuticals in a patient. More specifically, such continuous production can last for at least 1, 2, 3, 4, 5, 6, 7, 8, 9, 10, 11, 12, 13, or 14 days, at least 1, 2, 3, 4, 5, 6, 7, 8, 9, 10 weeks, or at least 1, 2, 3, 4, 5, 6, 7, 8, 9, 10, 11, or 12 months, or at least 1, 2, 3, 4, 5, 6, 7, 8, 9, 10 years. More specifically, such continuous production can last for at most 1, 2, 3, 4, 5, 6, 7, 8, 9, 10, 11, 12, 13, or 14 days, at least 1, 2, 3, 4, 5, 6, 7, 8, 9, 10 weeks, or at least 1, 2, 3, 4, 5, 6, 7, 8, 9, 10, 11, or 12 months, or at least 1, 2, 3, 4, 5, 6, 7, 8, 9, 10 years.

In specific aspects, provided herein are methods for treating cancer, such as acute myeloid leukemia (AML) in a subject by administering a therapeutic effective amount of SCs expressing an antibody, e.g., multispecific antibody, such as bispecific antibody and a T cell co-stimulatory ligand, such as the co-stimulatory 4-1BB ligand (CD137L). Also provided herein are related methods for inducing/enhancing T cell proliferation and related methods for activating T cells using such SCs.

In particular embodiments, provided herein are methods for managing, treating, preventing or protecting against AML in a subject (e.g. human subject) in need thereof, administering to the subject a therapeutically effective amount of SCs expressing an antibody, e.g., a multispecific antibody, such as a bispecific antibody (e.g. anti-CD33-anti-CD3 bispecific antibody), and a T cell co-stimulatory ligand, such as the co-stimulatory 4-1BB ligand (CD137L).

In a particular embodiment, provided herein is a method for inducing or enhancing T cell proliferation comprising T cells interacting with an effective amount of SCs expressing an antibody, e.g., multispecific antibody, such as bispecific antibody (for example, anti-CD33-anti-CD3 bispecific antibody), and a T cell co-stimulatory ligand, such as the co-stimulatory 4-1BB ligand (CD137L). In a specific embodiment, provided herein is a method for inducing or enhancing T cell proliferation in a subject in need thereof, comprising a therapeutic effective amount of SCs expressing an antibody, e.g., multispecific antibody, such as bispecific antibody (for example, anti-CD33-anti-CD3 bispecific antibody), and optionally a T cell co-stimulatory ligand, such as the co-stimulatory 4-1BB ligand (CD137L).

In particular embodiments, T cell proliferation is increased by at least 10%, 20%, 30%, 40%, 50%, 60%, 70%, 80%, 90%, 100%, 150%, 200%, 250%, 300%, 400%, or 500% or more in presence of SCs compared to their absence, as determined by methods known in the art, for example, those described herein.

In a particular embodiment, provided herein is a method for inducing or enhancing T cell activation, comprising T cells interacting with an effective amount of SCs expressing an antibody, e.g., multispecific antibody, such as bispecific antibody (for example, anti-CD33-anti-CD3 bispecific antibody), and a T cell co-stimulatory ligand, such as the co-stimulatory 4-1BB ligand (CD137L). In a specific embodiment, provided herein is a method for inducing or enhancing T cell activation in a subject in need thereof, comprising a therapeutic effective amount of SCs expressing an antibody, e.g., multispecific antibody, such as bispecific antibody (for example, anti-CD33-anti-CD3 bispecific antibody), and a T cell co-stimulatory ligand, such as the co-stimulatory 4-1BB ligand (CD137L).

In particular embodiments, T cell activation is increased by at least 10%, 20%, 30%, 40%, 50%, 60%, 70%, 80%, 90%, 100%, 150%, 200%, 250%, 300%, 400%, or 500% or more in presence of SCs compared to their absence, as determined by methods known in the art, for example, those described herein (e.g., Examples Section).

These and other objects, features, and advantages of this invention will become apparent from the following detailed description of the various aspects of the invention taken in conjunction with the accompanying drawings.

BRIEF DESCRIPTION OF THE DRAWINGS

For the purpose of illustrating aspects of the present invention, there are depicted in the drawings certain embodiments of the invention. However, the invention is not limited to the precise arrangements and instrumentalities of the embodiments depicted in the drawings. Further, as provided, like reference numerals contained in the drawings are meant to identify similar or identical elements.

FIG. 1A: Schematic representation of the structure of the bsab CD33-CD3 constructed as single-chain bispecific tandem fragment variable (scB-sTaFv). The VH and VL domains of each scFv were humanized by CDR grafting and connected via a linker comprised of three repeats of four glycine and one serine residues 3*(Gly4Ser). The N-terminus of the bsab construct contains a signal peptide (SP) for the secretion of the bsab into the cell culture medium, whereas its C-terminus tag harbors a myc- (myc) and his-tag (his) used for immunochemical Ab detection and purification. FIG. 1B: Schematic illustrating binding of the bsab to its target antigens CD3 and CD33 cross-links a T cell and a tumor cell and establishes an immune synapse. FIG. 1C: Transgene expression analysis of parental and transduced hMSCs was performed by flow cytometry. The percentages of living CD45− and EGFP+ cells are shown. Dead cells were excluded by propidium iodide staining. FIG. 1D: Purified fractions of the bsab CD33-CD3 secreted in the culture medium were separated on SDS-gels and thereafter stained either with Coomassie brilliant blue® or analyzed by Western blotting. FIG. 1E: The quantitative analysis of the released bsab was performed by ELISA. hMSCs cells were seeded at limiting cell densities and the antibody concentration [ng/ml] in culture medium was determined after 48 h of culture. Results represent the means±SD of two independent experiments.

FIG. 2A: CD33+ MOLM-13 cells (left panels) and T cells (right panels) were stained with either the maternal anti-CD33 and anti-CD3 mAbs following by a PE-conjugated anti-mouse IgG secondary Ab (black graphs) or the anti-CD33-anti-CD3 bsab and a FITC-labeled anti-myc Ab (black graphs). As controls, samples were stained with secondary antibodies alone (white graphs). FIG. 2B: BsAb binding to CD33− HEK293T cells or SCP-1 wt cells was analyzed in parallel by flow cytometry after staining with the bsab and the anti-myc/FITC Ab. FIG. 2C: The accessibility of the bsab to the CD33 antigen on MOLM-13 cells was tested after pretreatment with 2, 20 and 200 μg/ml of the maternal anti-CD33 mAb respectively.

FIG. 3A: HEK293T, OCI-AML3, U937 and MOLM-13 were analyzed for CD33 surface expression levels by staining with anti-CD33/PE mAb (in black) or matched isotype control Ab (in grey) respectively. Numbers represent mean fluorescence intensity (MFI) of total cells. FIG. 3B: In a standard chromium release assay 51Cr labeled CD33+ MOLM-13 cells and CD33− HEK293T cells were incubated with freshly isolated T cells at effector to target (e:t) cell ratio of 5:1 for 20 h with decreasing concentrations of the purified bsab CD33-CD3. Mean±SD of 2 independent donors is shown. FIG. 3C: Specific cell lysis of AML cell lines U937 (upper) and MOLM-13 (lower) measured with standard chromium release assay. Freshly isolated CD3+ T cells were co-cultured for 10 and 20 h with 51Cr labeled CD33+ target cells at an e:t cell ratio of 5:1 in the presence of hMSC lines seeded at different concentrations 48 h before adding effector T cells and target cells. Data are presented as means±SD from two or three different donors, respectively. FIG. 3D: Decreasing densities of 51Cr labeled gene-modified hMSCs were co-cultured with PBMCs in the presence or absence of CD33+ MOLM-13 cells at an e:t ratio of 5:1. After 20 h of co-incubation the specific hMSCs lysis was examined via chromium release assay. Data shown as mean±SD from two independent donors.

FIG. 4A: For the analysis of the 4-1BBL transgene expression hMSCs were stained with PE-conjugated anti-CD137L antibody and the surface expression of the immunoligand as well as intracellular EGFP signal correlating with bsab CD33-CD3 expression were analyzed by flow cytometry. Positive cells are shown as percentages of all analyzed cells. Dead cells were excluded by propidium iodide counter-staining. Quadrant position was placed based on isotype control staining (not shown). FIG. 4B: In a flow cytometry-based cytotoxicity assay eFluor670 proliferation dye-labeled CD33+OCI-AML3 cells were incubated with pan T cells at an e:t ratio of 1:1 for 24 h, 48 h (upper) and 96 h (lower) in the presence or absence of gene-modified hMSCs seeded at limiting densities 48 h prior to the experiment. Target cell numbers counted at the indicated time points were normalized to the control sample with only target cells. Data represent the means±SD of three different donors. Statistical significance was determined using one-way ANOVA with Bonferroni multiple comparison test. **p<0.01.

FIG. 5A: Secretion of pro-inflammatory cytokines by T cells was determined after 24 h culture upon their cross-linkage with the transgenic CD33-expressing HEK293T cells via hMSC-produced CD33-CD3 bsab in the presence or absence of the hMSC-presented co-stimulatory 4-1BBL. FIG. 5B: After 6 days of co-cultivation with target cells T cell counts were investigated and T cell expansion was calculated as ratio of T cell number at day 6 to T cell number seeded at day 0. Data are shown as means±SD of three or four individual donors. Statistical significance was determined using one-way ANOVA with Bonferroni multiple comparison test. *p<0.05; p<0.01; *p<0.001.

FIG. 6A: 1×105 AML patient-derived MNCs were cultured together with 48 h pre-seeded 1×104 hMSCs. After 96 h of co-cultivation the percentages of surviving HLA-DR+ AML blasts and CD3+ T cells were determined respectively as proportions of all CD45+ cells by flow cytometry analysis. FIG. 6B: Total AML blasts number after 24, 48 and 96 h of co-incubation was calculated. The average of surviving cells and the SD of triplets are shown for one representative donor out of three. FIG. 6C: Total numbers of CD3-CD123+HLA-DR+CD45+AML blasts (left) and CD3+CD123-HLA-DR-CD45+ T cells (right) after 96 h of co-cultivation with or without control/bsab- and 4-1BBL-expressing hMSCs are reported for three independent donors. Numbers of each subpopulation were calculated according to their relative percentages as determined by staining for specific cell surface markers. FIG. 6D: Absolute autologous T cell number was measured after 96 h and overall expansion of the cells in the presence of hMSCs was determined. Data are presented as means±SD from three different donors. Statistical significance was determined using one-way ANOVA with Bonferroni multiple comparison test. *p<0.05; p<0.01; *p<0.001.

DETAILED DESCRIPTION OF THE INVENTION

Figure 1A:
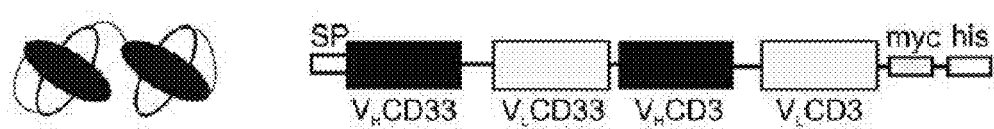
FIGS. 1A-1E: Generation of bsab CD33-CD3 releasing gene-modified hMSCs.

In a further aspect, provided herein are mesenchymal stem cells (MSCs), such as human MSCs (hMSCs), engineered to express an antibody, e.g., multispecific antibody, such as a bispecific antibody targeting CD33 and CD3, and, optionally, a human T cell co-stimulatory ligand, such as the human T cell co-stimulatory 4-1BB ligand (CD137L) or an active fragment thereof. In specific aspects, also provided herein are methods for treating acute myeloid leukemia (AML) using such hMSCs, as well as related methods for inducing/enhancing T cell proliferation and related methods for activating T cells.

In one aspect provided herein are human mesenchymal stem cells (hMSCs) engineered to express a multispecific antibody, such as a bispecific antibody targeting CD33 and CD3, and, optionally, a human T cell co-stimulatory ligand, such as the human T cell co-stimulatory 4-1BB ligand (CD137L) or an active fragment thereof. In specific aspects, also provided herein are methods for treating acute myeloid leukemia (AML) using such hMSCs, as well as related methods for inducing/enhancing T cell proliferation and related methods for activating T cells using such hMSCs.

In certain embodiments, the presently disclosed methods and uses enhance the T cell response against a cancer cell. Without being bound by theory, the improved T cell response against a cancer cell is accomplished by targeting of hMSCs to the cancer cell in a patient. In certain embodiments, at least $1 \times 10^5$, $2 \times 10^5$, $3 \times 10^5$, $4 \times 10^5$, $5 \times 10^5$, $6 \times 10^5$, $7 \times 10^5$, $8 \times 10^5$, $9 \times 10^5$, $1 \times 10^6$, $2 \times 10^6$, $3 \times 10^6$, $4 \times 10^6$, $5 \times 10^6$, $6 \times 10^6$, $7 \times 10^6$, $8 \times 10^6$, $9 \times 10^6$, or at least $1 \times 10^7$ MSCs as described herein are administered to a patient. In certain embodiments, at most $1 \times 10^5$, $2 \times 10^5$, $3 \times 10^5$, $4 \times 10^5$, $5 \times 10^5$, $6 \times 10^5$, $7 \times 10^5$, $8 \times 10^5$, $9 \times 10^5$, $1 \times 10^6$, $2 \times 10^6$, $3 \times 10^6$, $4 \times 10^6$, $5 \times 10^6$, $6 \times 10^6$, $7 \times 10^6$, $8 \times 10^6$, $9 \times 10^6$, or at least $1 \times 10^7$ MSCs as described herein are administered to a patient. In a more specific embodiment between $5 \times 10^6$ and $6 \times 10^6$ MSCs as described herein are administered to a patient.

In certain embodiments, at least 1 mg, 2 mg, 3 mg, 4 mg, 5 mg, 6 mg, 7 mg, 8 mg, 9 mg, or at least 10 mg cell mass of an MSC as described herein can be transplanted into a patient. In certain embodiments, at most 1 mg, 2 mg, 3 mg, 4 mg, 5 mg, 6 mg, 7 mg, 8 mg, 9 mg, or at least 10 mg cell mass of an MSC as described herein can be transplanted into a patient. In certain embodiments, about 1 mg, 2 mg, 3 mg, 4 mg, 5 mg, 5.5 mg, 6 mg, 7 mg, 8 mg, 9 mg, or at least 10 mg cell mass of an MSC as described herein can be transplanted into a patient.

MSCs can be used as in situ producer of anti-cancer therapeutics. In certain embodiments, autologous gene-modified MSCs as described herein can be injected intravenously into patients promoting their migration to the tumor site and the local delivery of their payload without being bound by theory. In other embodiments, MSCs could be trapped into an artificial scaffold matrix and transplanted subcutaneously in proximity of a tumor site. Again, without being bound by theory, thus the potential supportive role in tumor angiogenesis processes could be reduced, ensuring that transplanted MSCs cannot escape from their confined artificial environment. An additional benefit of this strategy can be that the delivery of the anti-cancer agent can be controlled and stopped after tumor clearance by removing the scaffold [Compte et al. (2007) Cancer Gene Ther: 14(4): 380-388.].

In certain embodiment, the use of MSCs to in situ production of anti-cancer therapeutics (eg, bispecific antibodies) results in continuous delivery of the anti-cancer therapeutic in a patient. More specifically, such continuous production can be production for at least 1, 2, 3, 4, 5, 6, 7, 8, 9, 10, 11, 12, 13, or 14 days, at least 1, 2, 3, 4, 5, 6, 7, 8, 9, 10 weeks, or at least 1, 2, 3, 4, 5, 6, 7, 8, 9, 10, 11, or 12 months, or at least 1, 2, 3, 4, 5, 6, 7, 8, 9, 10 years. More specifically, such continuous production can be production for at most 1, 2, 3, 4, 5, 6, 7, 8, 9, 10, 11, 12, 13, or 14 days, at least 1, 2, 3, 4, 5, 6, 7, 8, 9, 10 weeks, or at least 1, 2, 3, 4, 5, 6, 7, 8, 9, 10, 11, or 12 months, or at least 1, 2, 3, 4, 5, 6, 7, 8, 9, 10 years.

Mesenchymal Stem Cells

Any mesenchymal stem cells known to the skilled artisan can be used with the methods and compositions provided herein. For example, methods for isolating primary hMSCs have been described, see, e.g., Penfornis and Pochampally, 2011, Methods Mol Biol., 698:11-21; and Qiao et al., 2008, Cell Biol. International, 32: 8-15. Mesenchymal stem cells, or MSCs, are multipotent stromal cells that can differentiate into a variety of cell types, including bone, cartilage, and fat cells. MSCs can be derived from bone marrow.

In a specific aspect, provided herein are mesenchymal stem cells (MSCs), such as human MSCs (hMSCs), recombinantly expressing an antibody (e.g., multispecific antibody, such as bispecific antibody, for example, anti-CD33-anti-CD3 bispecific antibody), and optionally a T cell co-stimulatory ligand, such as the co-stimulatory 4-1BB ligand (CD137L).

In a particular aspect, hMSCs provided herein are engineered to express multispecific antibodies, e.g., bispecific antibodies (e.g., bispecific antibodies targeting CD33 and CD3) are derived from the single-cell-picked clone 1 (SCP-1) cell line (Böcker et al., 2008, J Cell Mol Med: 12: 1347-1359), derived from human mesenchymal stem cells and immortalized by lentiviral transduction of the gene coding for the human telomerase reverse transcriptase (hTERT).

In a certain aspect, hMSCs provided herein engineered to express multispecific antibodies, e.g., bispecific antibodies (e.g., bispecific antibodies targeting CD33 and CD3) are derived from primary hMSCs.

For the generation of permanent hMSCs expressing multispecific antibodies, e.g., bispecific antibodies (e.g., bispecific antibodies targeting CD33 and CD3), cDNA encoding a recombinant antibody (e.g., multispecific antibody, such as bispecific antibody, for example, anti-CD33-anti-CD3 bispecific antibody) construct can, for example, be cloned into a a viral vector (e.g., self-inactivating retroviral vector), such as a retroviral vector or lentiviral vector (e.g., p6NST50) to generate a transfer vector. In this viral vector, the expression of a recombinant antibody (e.g., multispecific antibody, such as bispecific antibody, for example, anti-CD33-anti-CD3 bispecific antibody) can be driven by a suitable promoter, such as a viral promoter, e.g., spleen focus forming virus (SFFV)-derived internal promoter. In certain embodiments, an enhanced green fluorescence protein (EGFP)-Zeocin fusion protein can be co-expressed by an internal ribosomal entry site (IRES). Lentiviral particles pseudotyped with an envelope protein, e.g., the Vesicular Stomatitis Virus envelope 120 (VSV-G), can be generated by transient transfection of a packaging cell, e.g., HEK293T cells, and virus supernatant are harvested and used to stably transduce hMSCs, such as SCP-1 cells.

For ectopic expression of a co-stimulary ligand, e.g., the co-stimulatory 4-1BB ligand (CD137L), on the surface of hMSCs, such as SCP-1 cells, a viral vector, such as a retroviral vector or a lentiviral vector, can be used which harbors an appropriate promoter, such as an internal minimal human elongation factor 1alpha promoter.

In a particular aspect, hMSCs can be co-transfected with two or more expression vectors (e.g., viral vectors) encoding polypeptides that associate (e.g., covalently or noncovalently) to form antigen binding domains (e.g., antigen-binding domains comprising a VH and a VL) of an antibody (e.g., multispecific antibody, such as bispecific antibody, for example, anti-CD33-anti-CD3 bispecific antibody) expressed by hMSCs.

In certain embodiments, at least 1 pg, 5 pg, 10 pg, 50 pg, 75 pg, 100 pg, 250 pg of antibody are produced per cell over a period of 48 hours. In other embodiments at most 1 pg, 5 pg, 10 pg, 50 pg, 75 pg, 100 pg, 250 pg of antibody are produced per cell over a period of 48 hours. In certain embodiments, 5-10, 5-50, 10-50, 25-75, or 8-70 pg of antibody are produced per cell over a period of 48 hours.

Antibodies

In specific aspects, provided herein are antibodies, such as bispecific antibodies, which are recombinantly expressed by hMSCs. In a particular embodiment, such bispecific antibodies target CD33, e.g., human CD33. In a specific embodiment, such bispecific antibodies target CD33, e.g., human CD33, and CD3, e.g., human CD3. In certain aspects, a bispecific antibody provided herein is a single chain bispecific antibody. In a particular embodiment, a bispecific antibody provided herein, such as a single chain bispecific antibody, is humanized (e.g., humanized bispecific antibody targeting CD33 and CD3).

As used herein, the terms "variable region" or "variable domain" refer to a portion of an antibody, generally, a portion of an antibody light or heavy chain, typically about the amino-terminal 110 to 120 amino acids in a mature heavy chain and about the amino-terminal 90 to 100 amino acids in a mature light chain. Variable regions comprise complementarity determining regions (CDRs) flanked by framework regions (FRs). Generally, the spatial orientation of CDRs and FRs are as follows, in an N-terminal to C-terminal direction: FR1-CDR1-FR2-CDR2-FR3-CDR3-FR4. Without wishing to be bound by any particular mechanism or theory, it is believed that the CDRs of the light and heavy chains are primarily responsible for the interaction of the antibody with antigen and for the specificity of the antibody for an epitope. In a specific embodiment, numbering of amino acid positions of antibodies described herein is according to the EU Index, as in Kabat et al. (1991) *Sequences of Proteins of Immunological Interest*, Fifth Edition, U.S. Department of Health and Human Services, NIH Publication No. 91-3242. In certain embodiments, the variable region is a human variable region. In certain embodiments, the variable region comprises murine (e.g., mouse or rat) CDRs and human framework regions (FRs). In particular embodiments, the variable region is a primate (e.g., human or non-human primate) variable region. In certain embodiments, the variable region comprises murine (e.g., mouse or rat) CDRs and primate (e.g., human or non-human primate) framework regions (FRs). As a non-limiting example, a variable region described herein is obtained from assembling two or more fragments of human sequences into a composite human sequence.

In certain aspects, the CDRs of an antibody can be determined according to (i) the Kabat numbering system (Kabat et al. (1971) *Ann. NY Acad. Sci.* 190:382-391 and, Kabat et al. (1991) *Sequences of Proteins of Immunological Interest*, Fifth Edition, U.S. Department of Health and Human Services, NIH Publication No. 91-3242); or (ii) the Chothia numbering scheme, which will be referred to herein as the "Chothia CDRs" (see, e.g., Chothia and Lesk, 1987, J. Mol. Biol., 196:901-917; Al-Lazikani et al., 1997, J. Mol. Biol., 273:927-948; Chothia et al., 1992, J. Mol. Biol., 227:799-817; Tramontano A et al., 1990, J. Mol. Biol. 215(1):175-82; and U.S. Pat. No. 7,709,226); or (iii) the ImMunoGeneTics (IMGT) numbering system, for example, as described in Lefranc, M.-P., 1999, The Immunologist, 7:132-136 and Lefranc, M.-P. et al., 1999, Nucleic Acids Res., 27:209-212 ("IMGT CDRs"); or (iv) MacCallum et al., 1996, J. Mol. Biol., 262:732-745. See also, e.g., Martin, A., "Protein Sequence and Structure Analysis of Antibody Variable Domains," in *Antibody Engineering*, Kontermann and Dübel, eds., Chapter 31, pp. 422-439, Springer-Verlag, Berlin (2001).

In a specific aspect, provided herein are hMSCs expressing multispecific antibodies, e.g., bispecific antibodies, such as single chain bispecific antibodies, comprising a VL and a VH targeting CD33 (e.g., human CD33). In specific aspects, multispecific antibodies, such as, bispecific antibodies, e.g., single chain bispecific antibodies, described herein comprise one or more linkers (e.g., one, two, three, four, or five, or more linkers). In a certain embodiment, such a linker described herein comprises repetitions, for example, at least one, two, three, four or five repetitions, of glycine-serine, e.g., G4S linkers. In certain specific embodiments, a bispecific antibody for use with the methods and compositions disclosed herein consists of or comprises the following structure: (humanized heavy chain variable region of anti-CD33)-(G4S)3-(humanized light chain variable region of anti-CD33)-AAARG (SEQ ID NO:1)-(humanized heavy chain variable region of anti-CD3)-(G4S)3-(humanized light chain variable region of anti-CD3). In certain even more specific embodiments, such a bispecific antibody further comprises at its N-terminus a signal peptide suitable for secretion of the bispecific antibody from the hMSC and/or an AAQPA (SEQ ID NO:2) sequence between the signal peptide and the humanized heavy chain variable region of anti-CD33; and/or a myc tag at the C-terminus; and/or a histidine tag at the C-terminus.

Non-limiting examples of antibodies comprising a VL and a VH targeting CD33 have been described, for example, U.S. Patent Application Publication No. US 2012/0251554 A1 (e.g., antibodies comprising CDRs of anti-CD33 antibody DRB1 or DRB2); Stamova et al., 2011, Molecular Immunol., 49: 474-482; Arndt et al., 2013, Leukemia, 27: 964-967; and Arndt et al., 2014, Leukemia, 28: 59-69, each of which is incorporated herein by reference in its entirety.

In a specific embodiment, provided herein are hMSCs expressing a multispecific antibody, e.g., bispecific antibody, such as a single chain bispecific antibody, which specifically binds to CD33 (e.g., human CD33) comprising a heavy chain variable region (VH) and a light chain variable region (VL), wherein (i) the VH comprises complementarity determining region CDR1 comprising the amino acid sequence DYVVH (SEQ ID NO:3), CDR2 comprising the amino acid sequence YINPYNDGTKYNEKFKG (SEQ ID NO:4), and CDR3 comprising the amino acid sequence DYRYEVYGMDY (SEQ ID NO:5); and (ii) the VL comprises CDR1 comprising the amino acid sequence TASSSVNYIH (SEQ ID NO:6), CDR2 comprising the amino acid sequence TSKVAS (SEQ ID NO:7), and CDR3 comprising the amino acid sequence QQWRSYPLT (SEQ ID NO:8).

In a specific embodiment, provided herein are hMSCs expressing a multispecific antibody, e.g., bispecific antibody, such as a single chain bispecific antibody, which specifically binds to CD33 (e.g., human CD33) comprising a heavy chain variable region (VH) and a light chain variable region (VL), wherein (i) the VH comprises CDR1, CDR2 and CDR3 comprising amino acid sequences as set forth in Table 1; and (ii) the VL comprises CDR1, CDR2 and CDR3 comprising amino acid sequences as set forth in Table 2.

TABLE 1

VH CDRs of representative anti-CD33 antibodies

| VH CDR1 | VH CDR2 | VH CDR3 |
| --- | --- | --- |
| SYYIH (SEQ ID NO: 9) | VIYPGNDDISYNQKFXG (SEQ ID NO: 13) | EVRLRYFDV (SEQ ID NO: 17) |
| DYNMH (SEQ ID NO: 10) | YIYPNGGTGYNQKFKS (SEQ ID NO: 14) | GRPAMDY (SEQ ID NO: 18) |
| DYNMY (SEQ ID NO: 11) | YIDPYKGGTIYNQKFKG (SEQ ID NO: 15) | QMITAYYFDY (SEQ ID NO: 19) |
| DYVLH (SEQ ID NO: 12) | LINTYNGDVRYNQKFMG (SEQ ID NO: 16) | DYRYEYYAMDY (SEQ ID NO: 20) |

TABLE 2

VL CDRs of representative anti-CD33 antibodies

| VL CDR1 | VL CDR2 | VL CDR3 |
| --- | --- | --- |
| KSSQSVFFSSSQKNYLA (SEQ ID NO: 21) | WASTRES (SEQ ID NO: 25) | HQYLSSRT (SEQ ID NO: 29) |
| RASESVDNYGISFMN (SEQ ID NO: 22) | ASNQGS (SEQ ID NO: 26) | QQSKEVPWT (SEQ ID NO: 30) |
| KASQDINKYIA (SEQ ID NO: 23) | TSTLQP (SEQ ID NO: 27) | LQYDNLLT (SEQ ID NO: 31) |
| SANSSVSYIH (SEQ ID NO: 24) | TSKLAS (SEQ ID NO: 28) | QQWTSHPLT (SEQ ID NO: 32) |

In a specific aspect, provided herein are hMSCs expressing multispecific antibodies, e.g., bispecific antibodies, such as single chain bispecific antibodies, comprising (i) a VL and a VH targeting CD33 (e.g., human CD33) and (ii) a VL and a VH targeting CD3 (e.g., human CD3).

Non-limiting examples of antibodies comprising a VL and a VH targeting CD3 have been described, for example, U.S. Pat. Nos. 7,728,114 and 5,929,212; and PCT International Patent Application Publication Nos. WO 2014/047231 and WO 2004/108158; each of which is incorporated herein by reference in its entirety.

In a specific embodiment, provided herein are hMSCs expressing a multispecific antibody, e.g., bispecific antibody, such as a single chain bispecific antibody, which specifically binds to CD33 (e.g., human CD33) and CD3 (e.g., human CD3), comprising a heavy chain variable region (VH) and a light chain variable region (VL) of a humanized antibody which specifically binds to human CD33, wherein (i) the VH comprises complementarity determining region CDR1 comprising the amino acid sequence DYVVH (SEQ ID NO:3), CDR2 comprising the amino acid sequence YINPYNDGTKYNEKFKG (SEQ ID NO:4), and CDR3 comprising the amino acid sequence DYRYEVYGMDY (SEQ ID NO:5); and (ii) the VL comprises CDR1 comprising the amino acid sequence TASSSVNYIH (SEQ ID NO:6), CDR2 comprising the amino acid sequence TSKVAS (SEQ ID NO:7), and CDR3 comprising the amino acid sequence QQWRSYPLT (SEQ ID NO:8). Non-limiting examples of fully humanized anti-CD33-anti-CD3 bispecific antibodies have been described, e.g., see Arndt et al., 2013, Leukemia, 27: 964-967.

In a specific embodiment, an anti-CD33-anti-CD3 bispecific antibody has the following configuration from the N-terminus to the C-terminus: heavy chain variable region targeting CD33 (VH/CD33)-linker1-light chain variable region targeting CD33 (VL/CD33)-linker2-heavy chain variable region targeting CD3 (VH/CD3)-linker3-light chain variable region targeting CD3 (VL/CD3).

In certain embodiments, the CDRs for the anti-CD3 portion of a multispecific or bispecific antibody are the CDRs of MT-301 (see, e.g., Arndt et al. 2014, Leukemia 28:59-69).

In specific embodiments, multispecific antibodies, such as, bispecific antibodies, e.g., single chain bispecific antibodies, described herein comprises at the N-terminus, a signal peptide, e.g., an Ig leader sequence as signal peptide, for protein secretion.

In certain embodiments, multispecific antibodies, such as, bispecific antibodies, e.g., single chain bispecific antibodies, described herein comprises at the C-terminus a tag, for example, myc-tag or and histidine (his)-tag (e.g, 6×his-tag) for protein purification and/or detection.

In certain embodiments, antibodies (e.g., multispecific antibodies, such as bispecific antibodies) described herein can be of any type (e.g., IgG, IgE, IgM, IgD, IgA or IgY), any class, (e.g., IgG$_1$, IgG$_2$, IgG$_3$, IgG$_4$, IgA$_1$ or IgA$_2$), or any subclass (e.g., IgG$_{2a}$ or IgG$_{2b}$, or a mixture thereof) of immunoglobulin molecule.

In specific embodiments, multispecific antibodies, such as, bispecific antibodies, e.g., single chain bispecific antibodies, described herein do not comprise an antibody constant region.

Methods for making multispecific (e.g, bispecific antibodies) have been described, see, for example, U.S. Pat. Nos. 7,951,917, 7,183,076, 8,227,577, 5,837,242, 5,989,830, 5,869,620, 6,132,992, and 8,586,713.

Ligands of Co-Stimulatory Molecules

In a specific aspect, provided herein are hMSCs that recombinantly express an antibody (e.g., multispecific antibody, such as bispecific antibody, for example, anti-CD33-anti-CD3 bispecific antibody), and optionally a T cell co-stimulatory ligand, such as the co-stimulatory 4-1BB ligand (CD137L).

Non-limiting examples of co-stimulatory receptors having ligands, which can be recombinantly expressed on the cell surface of hMSCs provided herein include, but are not limited to, those described in Table 3, e.g., CD28 ligand B7-1 and B7-2, Ox40L ligand OX40L, CD27 ligand CD70 (CD27L), LFA-1 ligand ICAM-1, -2, and -3, and SLAM ligand.

TABLE 3

Co-Stimulatory Receptors

| Co-stimulatory Molecule | Description | Genbank Accession No. |
| --- | --- | --- |
| 4-1BB (CD137) | (Watts & DeBenedette, Current Opinion in Immunology, 1999. 11: 286-293). | U03397.1 |
| CD28 | CD28 is the primary co-stimulatory receptor for inducing high level IL-2 production and survival of naive CD4+ T cells.<br>Ligand: B7-1 and B7-2<br>(Watts & DeBenedette, Current Opinion in Immunology, 1999. 11: 286-293). | J02988.1 |
| Ox40 (CD134) | Promotes Th2 response; Sustains proliferation of Th1 and Th2 effectors; Enhances IL-2 and Th2 cytokine production; Up regulated on CD4+ T cells<br>Ligand: OX40L<br>(Watts & DeBenedette, Current Opinion in Immunology, 1999. 11: 286-293). | S76792.1 |
| CD27 | CD27 is a tumor necrosis factor receptor; Functions in T cell-B cell and T cell-T cell interations; Role in expansion of T cells after CD28 co-stimulation.<br>Ligand: CD70 (CD27L)<br>(Watts & DeBenedette, Current Opinion in Immunology, 1999. 11: 286-293). | NM_001242.4 |
| CD40 ligand (CD154) | Primarily expressed on activated T cells, acts as a costimulatory molecule<br>van Kooten C, Banchereau J (2000). "CD40-CD40 ligand". *J. Leukoc. Biol.* 67 (1): 2-17. | NG_007279.1 |
| ICOS Ligand | Inducible T-cell Costimulator (CD278) is a CD28-superfamily costimulatory molecule that is expressed on activated T cells.<br>(Watts & DeBenedette, Current Opinion in Immunology, 1999. 11: 286-293). | NM_012092.3 |
| LFA-1 | Lymphocyte function-associated antigen 1; Adhesion and cytoskeleton reorganization during T cell activation.<br>Ligand: ICAM-1, -2, -3<br>Watts & DeBenedette, Current Opinion in Immunology, 1999. 11: 286-293). | NM_001114380.1 |
| SLAM | Signaling lymphocytic activation molecule. SLAM is a CD2-related surface receptor expressed by activated T cells and B cells.<br>(Henning, Eur J Immunol. 2001 Sep; 31(9): 2741-50; Watts & DeBenedette, Current Opinion in Immunology, 1999. 11: 286-293).<br>Ligand: SLAM | AY040554.1 |

TABLE 3-continued

Co-Stimulatory Receptors

| Co-stimulatory Molecule | Description | Genbank Accession No. |
|---|---|---|
| 2B4 (CD244) | cell surface receptor expressed on natural killer cells (NK cells) and T cells mediating non-major histocompatibility complex (MHC) restricted killing. Latchman Y, McKay PF, Reiser H (1998) "Identification of the 2B4 molecule as a counter-receptor for CD48". *J. Immunol.* 161 (11): 5809-12. | BC028073.1 |

Uses and Methods

In specific aspects, provided herein are methods for treating cancer, such as acute myeloid leukemia (AML) in a subject by administering a therapeutically effective numbers of hMSCs expressing an antibody, e.g., multispecific antibody, such as bispecific antibody (for example, anti-CD33-anti-CD3 bispecific antibody), and optionally a T cell co-stimulatory ligand, such as the co-stimulatory 4-1BB ligand (CD137L). In certain embodiments, the cancer is a type of cancer associated with expression of CD33, such as AML, and one binding domain of the multispecific antibody is an anti-CD33 antibody. Also provided herein are related methods for inducing/enhancing T cell proliferation and related methods for activating T cells using such hMSCs.

In particular embodiments, provided herein are methods for managing, treating, preventing or protecting against AML in a subject (e.g., human subject) in need thereof, comprising administering to the subject a therapeutically effective amount of hMSCs expressing an antibody, e.g., multispecific antibody, such as bispecific antibody (for example, anti-CD33-anti-CD3 bispecific antibody), and optionally a T cell co-stimulatory ligand, such as the co-stimulatory 4-1BB ligand (CD137L).

In a particular embodiment, provided herein is a method for inducing or enhancing T cell proliferation comprising contacting T cells with an effective amount of hMSCs expressing an antibody, e.g., multispecific antibody, such as bispecific antibody (for example, anti-CD33-anti-CD3 bispecific antibody), and optionally a T cell co-stimulatory ligand, such as the co-stimulatory 4-1BB ligand (CD137L). In a specific embodiment, provided herein is a method for inducing or enhancing T cell proliferation in a subject in need thereof, comprising a therapeutic effective amount of hMSCs expressing an antibody, e.g., multispecific antibody, such as bispecific antibody (for example, anti-CD33-anti-CD3 bispecific antibody), and optionally a T cell co-stimulatory ligand, such as the co-stimulatory 4-1BB ligand (CD137L).

In particular embodiments, T cell proliferation is increased by at least 10%, 20%, 30%, 40%, 50%, 60%, 70%, 80%, 90%, 100%, 150%, 200%, 250%, 300%, 400%, or 500% or more in the presence of hMSCs secreting an antibody and optionally a T cell co-stimulatory ligand, as compared to unmodified hMSC or in the absence of hMSCs as determined by methods known in the art, for example, those described herein (e.g., Examples Section).

In a particular embodiment, provided herein is a method for inducing or enhancing T cell activation, comprising T cells stimulated by an effective amount of hMSCs expressing an antibody, e.g., multispecific antibody, such as bispecific antibody (for example, anti-CD33-anti-CD3 bispecific antibody), and optionally a T cell co-stimulatory ligand, such as the co-stimulatory 4-1BB ligand (CD137L). In a specific embodiment, provided herein is a method for inducing or enhancing T cell activation in a subject in need thereof, comprising a therapeutic effective amount of hMSCs expressing an antibody, e.g., multispecific antibody, such as bispecific antibody (for example, anti-CD33-anti-CD3 bispecific antibody), and optionally a T cell co-stimulatory ligand, such as the co-stimulatory 4-1BB ligand (CD137L).

In particular embodiments, T cell activation is increased by at least 10%, 20%, 30%, 40%, 50%, 60%, 70%, 80%, 90%, 100%, 150%, 200%, 250%, 300%, 400%, or 500% or more in the presence of hMSCs secreting an antibody and optionally a T cell co-stimulatory ligand as compared to unmodified hMSC or in the absence of hMSCs, as determined by methods known in the art, for example, those described herein (e.g., Examples Section).

EXAMPLES

The examples in this section are offered by way of illustration, and not by way of limitation.

Example 1

Bispecific antibodies (bsabs) engaging T cells against cancer cells are an emerging promising immunotherapeutic tool for the treatment of leukemia and solid tumors. Due to their low molecular mass, bsabs have a short half-life and have to be continuously infused in patients over prolonged time spans of several weeks to achieve clinical responses. As an alternative to continuous intravenous infusion through extra-corporal medical devices the use of mesenchymal stem cells (MSCs) as autonomous cellular machines for the production and secretion of bsabs.

A humanized anti-CD33-anti-CD3 bsab which is capable to redirect human T-cells against CD33 expressing leukemic cells was expressed in the immortalized human MSC line SCP-1. See, Stamova S, et al. (2011) Leukemia: 25[6]: 1053-1056; Stamova S, et al. (2012) Anal Biochem: 423[2]: 261-268; Arndt C, et al. (2011) Blood: 118: 663-664; Arndt C, et al. (2013) Blood: 122[21]: 930; Arndt C, et al. (2013) Leukemia: 27: 964-967. Gene-modified SCP-1 cells expressed the bsab at sufficient amounts to redirect T cells efficiently against CD33 presenting target cells both in vitro as well as in an immunodeficient mouse model. The killing effect was independent of the antigen density on target cells. Moreover, T cells from patients suffering from acute myeloid leukemia (AML) in blast crisis eliminated autologous leukemic cells over time in the presence of the bsab secreting MSCs. The immune response against AML cells could be further enhanced by providing T cells an additional co-stimulus via the CD137-CD137 ligand axis through CD137L expression on MSCs.

T-cell engaging bispecific antibodies (bsabs) have been described. See, e. g., Stamova S, et al. (2012), Antibodies: 1[2]: 172-198; Stamova S, et al. (2011), Leukemia: 25[6]: 1053-1056; Feldmann A, et al. (2012), J Immunol: 189[6]: 3249-3259; Bargou R, et al. (2008), Science: 321[1]: 974-977; Handgretinger R, et al. (2011), Leukemia: 25: 181-184; Schlereth B, et al. (2006) Cancer Immunol Immunother 55[5]: 503-514; Stork R, et al. (2008) J Biol Chem: 283[12]: 7804-7812. Human mesenchymal stem cells (MSCs) have been described [Hamada H, et al. (2005) Cancer Sci: 96[3]: 149-156; Compte M, et al. (2013) Biomatter: 3[1]: e-pub doi: 10.4161/biom.23897]. Without being bound by theory MSCs have a limited immunogenicity and are even poorly recognized by HLA incompatible hosts [Le Blanc K, et al. (2003) Exp Hematol: 31[10]: 890-896; Götherström C, et al. (2004) Am J Obstet Gynecol: 190[1]: 239-245; Uccelli A, et al. (2008) Autoimmunity: 41[8]: 592-595] and have a tendency to accumulate at the site of tumors including metastatic lesions [Ren C, et al. (2008) Stem Cells: 26[9]: 2332-2338; Kim S M, et al. (2008) Cancer Res: 68[23]: 9614-9623; Uchibori R, et al. (2009) J Gene Med: 11[5]: 373-381]. Further, without being bound by theory, adoptive transfer of MSCs may provide an immunosuppressive environment helpful to reduce GvHD reactions [e. g. von Bonin M, et al. (2009) Bone Marrow Transplant: 43[3]: 245-251; Wehner R, et al. (2009) Haematologica: 94[8]: 1151-1156].

CD33 is predominantly expressed on myeloid-derived cells and found overexpressed on bone marrow cells from patients with AML as well as leukemic stem cells [Ehninger A, et al. (2014) Blood Cancer Journal: 4, e218: doi: 10.1038/bcj.2014.39]. Current conventional AML therapies do not achieve long-term remissions depending on age and subtype of the disease, therefore new adjuvant therapeutic strategies are urgently needed, especially for the elimination of minimal residual disease (MRD). It is demonstrated herein that gene-modified MSCs are able to (i) express the CD33-CD3 specific bsab at high levels, and (ii) mediate an efficient lysis of AML blasts by human primary T-cells from both healthy donors and AML patients.

Cell Lines

The human acute myeloid leukemia (AML) cell lines U937 (ACC 5) and MOLM-13 (ACC 554) were cultured in RPMI 1640 medium containing 10% of fetal calf serum (FCS, Biochrom AG), 100 μg/ml penicillin/streptomycin (Biochrom AG), whereas OCI-AML3 (ACC 582), HEK293T (ACC 635) and HEK293T genetically modified to ectopically express CD33 [Arndt C, et al. (2011) Blood: 118: 663-664] were cultured in DMEM medium (10% FCS, 100 μg/ml penicillin/streptomycin). The recently described single-cell-picked clone 1 (SCP-1) cell line [Böcker W, et al. (2008) J Cell Mol Med: 12[4]: 1347-1359], derived from human mesenchymal stem cells and immortalized by lentiviral transduction of the gene coding for the human telomerase reverse transcriptase (hTERT), were grown in RPMI 1640 medium (10% FCS, 100 μg/ml penicillin/streptomycin). All cell lines were maintained at 37° C. and 5% CO2.

Generation of Recombinant bsab-releasing hMSCs

The development of the fully humanized anti-CD33-anti-CD3 bsab is already described [Arndt C, et al. (2013) Leukemia: 27: 964-967]. For the generation of permanent hMSCs releasing the bsab, the cDNA encoding the recombinant Ab construct was cloned into the lentiviral vector p6NST50 [Koristka S, et al. (2013) J Autoimmun: 42: 105-116] to generate the transfer vector p6NST50.bsab.EGFP-Zeo. In this self-inactivating lentiviral vector, the expression of the CD33-CD3 bsab is driven by a spleen focus forming virus (SFFV)-derived internal promoter. An enhanced green fluorescence protein (EGFP)-Zeocin fusion protein is co-expressed by an internal ribosomal entry site (IRES). Lentiviral particles pseudotyped with the Vesicular Stomatitis Virus envelope (VSV-G) were generated by transient transfection of HEK293T cells and virus supernatant was harvested as recently described [Cartellieri M, et al. (2014) PLoS One: 9[4]: e93745. doi: 10.1371/journal.pone.0093745] and used to stably transduce SCP-1 cells. For the ectopic expression of the co-stimulatory 4-1BB ligand (CD137L) on SCP-1 cell surface a lentiviral vector was used which harbors an internal minimal human elongation factor 1alpha promoter instead of the SFFV promoter.

Flow-cytometry Analysis

Transduced and parental wild type cells were stained with anti-CD45/VioBlue, anti-CD33/PE, anti-CD90/VioBlue, anti-CD105/PE and anti-CD73/APC (all Miltenyi Biotec, Bergisch-Gladbach, Germany) monoclonal antibodies (mAbs) to analyze the hMSC marker profile. To monitor for 4-1BBL transgene expression SCP-1 cells were stained with an anti-CD137L/PE (BD Bioscience, Heidelberg, Germany) mAb. Cells stained only with matched isotype control Ab (in grey) served as negative control. Samples were analyzed using a MACSQuant Analyzer® and MACSQuantify software (both Miltenyi Biotec).

Expression, Purification and Quantitative Analysis of the Recombinant bsab

Culture supernatants of the stably transduced hMSCs were analyzed by sodium dodecyl sulfate-polyacrylamide gel electrophoresis (SDS-PAGE) for the His-tagged anti-CD33-anti-CD3 bsab purified by a single-step affinity chromatography on Ni-NTA columns (Qiagen, Hilden, Germany), and Western blotting using anti-penta-his mAb (Qiagen) and an alkaline phosphatase (AP)-coupled anti-mouse IgG antibody (Dianova, Hamburg, Germany) as previously described [e. g. Feldmann A, et al. (2011) Prostate: 71[9]: 998-1011]. The amount of anti-CD33-anti-CD3 bsab secreted was quantified by enzyme-linked immunosorbent assay (ELISA) as follow: SCP-1 cells were seeded as triplets in 96-well plates at decreasing cell densities. After 48 h of culture the supernatant of each sample was collected and added at a defined dilution to the wells of F16 MaxiSorp ELISA plates (Nunc), beforehand coated with 1.5 μg/ml mouse anti-pentaHis capture antibody (Qiagen), capable of binding the C-terminal histidine (his)-tag of the CD33-CD3 bsab. Standard samples were prepared as a 2-fold serial dilution from purified CD33-CD3 bsab (GEMoaB, Dresden, Germany) starting from 100 ng/ml. For binding of the captured bsab, a detection solution was prepared by diluting anti-Myc-HRP detection Ab (Miltenyi) 1:1000 in blocking buffer, and added to the samples for 2 h at RT. The substrate solution containing 100 μg/ml TMB, 10% DMSO, 0.05 M phosphate/citrate buffer and 30% $H_2O_2$ was added per well for 15 min to develop a color reaction and stopped by adding 1 M $H_2SO_4$ stop solution. The optical density was measured at 450 nm using the SUNRISE™ Microplate Reader (Tecan, Maennedorf, Switzerland) and used to calculate the concentration of hMSC-released bsab. Indirect immunofluorescence analysis was performed to examine the binding properties of the hMSCs-released bsab. A total of $5 \times 10^5$ CD33$^+$ or CD33$^-$ cell lines and PBMCs were stained with 20 μg/ml of the purified bsab. The bispecific construct was detected by flow cytometry using FITC-conjugated antibody against the myc-tag (Miltenyi) [Feldmann A, et al. (2012) J Immunol: 189[6]: 3249-3259; Feldmann A, et al. (2011) Prostate: 71[9]: 998-1011]. CD3$^+$ T cells were discriminated using an anti-CD3/VioBlue mAb, whereas anti-CD56/APC (Miltenyi) and anti-16/PE (BD Biosciences) mAbs were used to identify CD3-CD56$^+$ CD16$^+$ NK cells. Maternal anti-CD33 and anti-CD3 mAbs were used as control and detected with a PE-conjugated Goat F(ab)$_2$ anti-Mouse IgG (Fcgamma) Ab (Immunotech, Marseille, France).

T Cells Isolation from Human Healthy Donors

Human peripheral blood mononuclear cells (PBMCs) isolated from buffy coats of healthy volunteers after their informed consent were prepared by gradient centrifugation over polydextran based separating solution Biocoll (Biochrom). Pan T cells were freshly isolated from PBMCs by negative selection using the pan T cell isolation kit (Miltenyi Biotec), human CD4$^+$ and CD8$^+$ T cells by negative selection using the CD4$^+$ and CD8$^+$ T cell isolation kit (Miltenyi Biotec), respectively. Human T cells were cultured in RPMI 1640 medium containing 10% of fetal calf serum (FCS, Biochrom AG), 100 µg/ml penicillin/streptomycin (Biochrom AG), and 50 U/ml IL-2 (ImmunoTools, Friesoythe, Germany) overnight before starting the experiments the next day. T cells were washed twice with RPMI 1640 medium without any additives before added to the experimental cultures.

$^{51}$Cr-release and Flow-cytometry Based Cytotoxicity Assay

The killing of CD33$^+$ target tumor cells by T-cells redirected via hMSCs-released anti-CD33-anti-CD3 bsab was examined either by standard $^{51}$Cr release assays or by flow cytometry-based assays as recently established [Cartellieri M, et al. (2014) PLoS One: 9[4]: e93745. doi: 10.1371/journal.pone.0093745; Feldmann A, et al. (2011) Prostate: 71[9]: 998-1011; Koristka S, et al. (2012) J Immunol: 188[3]: 1551-1558].

Determination of Cytokine Concentration

To determine amounts of secreted IFN-γ, IL-10, TNF-α, and IL-2 from co-cultures, cell-free supernatants were collected at the indicated time and analyzed for cytokine secretion using OptEIA ELISA Sets (BD Biosciences) according to the manufacturer's protocol. The absorption of the samples was measured after 30 min, and the obtained values were used to calculate the concentration of the cytokines in the samples, according to the values obtained for the standard series provided by the manufacturer.

T-cell Activation and Proliferation Assays

The expression of the activation markers CD69 and CD25 were analyzed to determine the activation state of T cells. As target cells 1×10$^4$ transgenic CD33-expressing HEK293T cells were co-cultured with 5×10$^4$ untouched pan T cells in the presence or absence of 1×10$^4$ SCP-1 cells seeded 48 h before starting the experiment. After indicated time points, supernatant of each sample was collected and the cells of one triplet were pooled and stained with a mixture of anti-CD3/VioBlue, anti-CD69/FITC, anti-CD4/PerCP (all purchased from Miltenyi) and anti-CD25/PE (BD Biosciences). T cell proliferation assays were performed as previously described [Koristka S, et al. (2013) J Autoimmun: 42: 105-116; Koristka S, et al. (2012) J Immunol: 188[3]: 1551-1558].

Flow-cytometry Killing Assay with Fresh AML Samples

Mononuclear cell (MNC) samples from AML patients with hyperleukocytosis were obtained from leukapheresis products with informed consent and approval by the local institutional review board. MNCs were prepared by gradient centrifugation over polydextran based separating solution Biocoll (Biochrom). The redirection of autologous T cell towards AML blasts by the bsabs CD33-CD3-releasing hMSCs was investigated by co-cultivation of 1×10$^4$ 48 h pre-cultured genetically modified hMSCs with 1×10$^5$ AML patient-derived MNCs. The specific killing of myeloid cells was analyzed with MACSQuant® Analyzer (Miltenyi Biotec) at indicated time points. Moreover, MNCs of one triplet were pooled and stained with a mixture of anti-CD3/PECy7, anti-CD4/PerCP mAbs (Miltenyi) in order to analyze the relative percentage of T cells; and anti-CD123/PE, anti-HLA-DR/FITC and anti-CD45/VioBlue mAbs (Miltenyi Biotec) to discriminate the myeloid cell populations. Living cells were identified by being propidium iodide negative.

Mouse Model

NOD/SCID IL2Rγ−/− (NSG) mice were kept under standardized environmental conditions and received autoclaved food, water, and bedding. Prior to the injection, bsab-releasing or vector control containing hMSCs (5×10$^3$) were cultured for 48 hours and subsequently incubated together with 1×10$^5$ MOLM-13 cells and freshly isolated human T cells at an e:t ratio of 5:1. Following additional 24 hours of co-culture the mixed cell population was administrated intravenously (i.v.) to two groups of eight- to ten-week-old NSG mice via the tail vein. One group (5 animals) received MOLM-13 cells, T cells and vector control hMSCs, whereas the other group (4 animals) was treated with MOLM-13 cells, T cells and bsab-secreting hMSCs. Mice were daily monitored for posture, activity, fur texture and skin integrity. Animals were sacrificed according to local ethical committee guidelines when displayed pathological score and more than 15% body weight loss. The survival rate of bsab-treated or untreated mice was determined.

Statistical Analysis

Statistical analysis was performed using GraphPad Prism Software (La Jolla, Calif., USA). One-way analysis of variance (ANOVA) with Bonferroni Multiple Comparison test was used for statistical significance when multiple experiments were compared. Survival data were analyzed by using a Kaplan-Meier survival analysis with a log rank method of statistics (*$P<0.001$, $P<0.01$, *$P<0.05$).

Figure 1B:
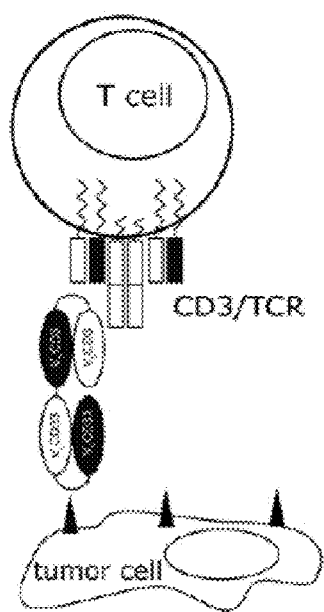
Figure 1C:
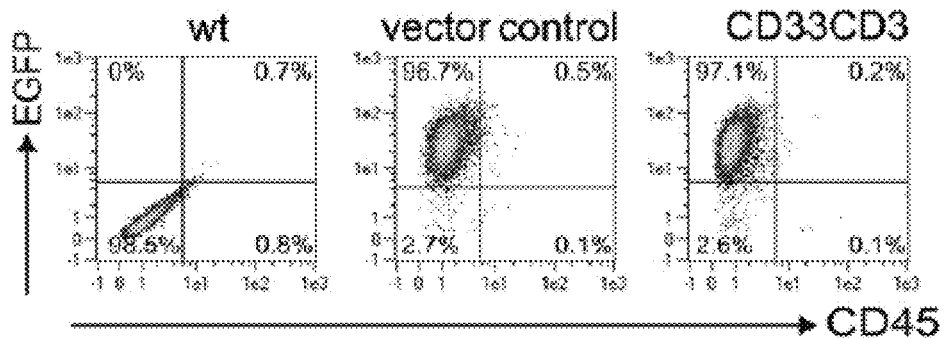
Figure 1D:
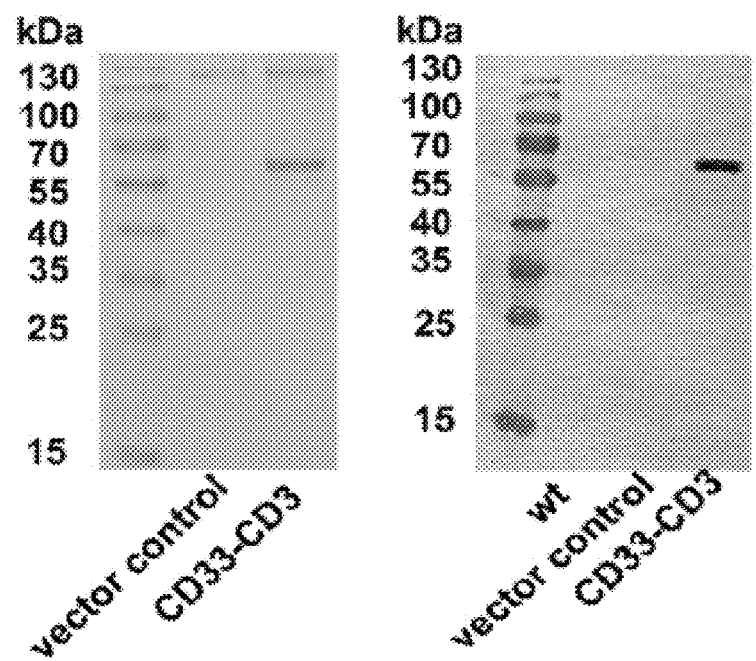
Figure 1E:
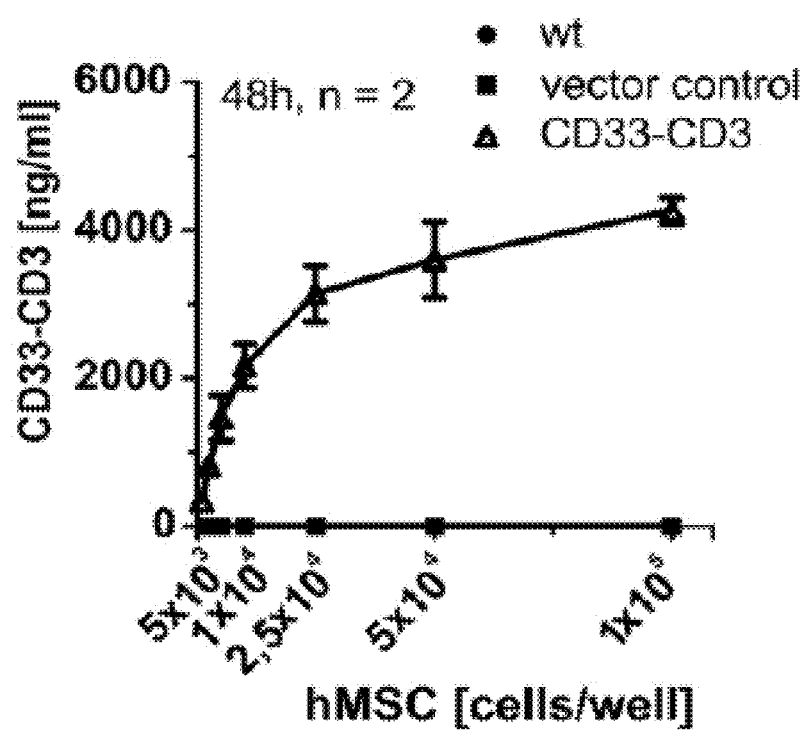
Figure 2A:
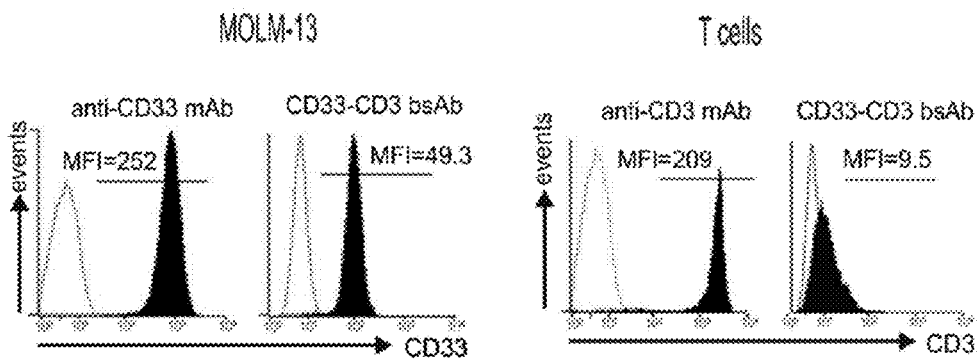
FIGS. 2A-2C: Antigen binding properties of the hMSC secreted recombinant protein.
Figure 2B:
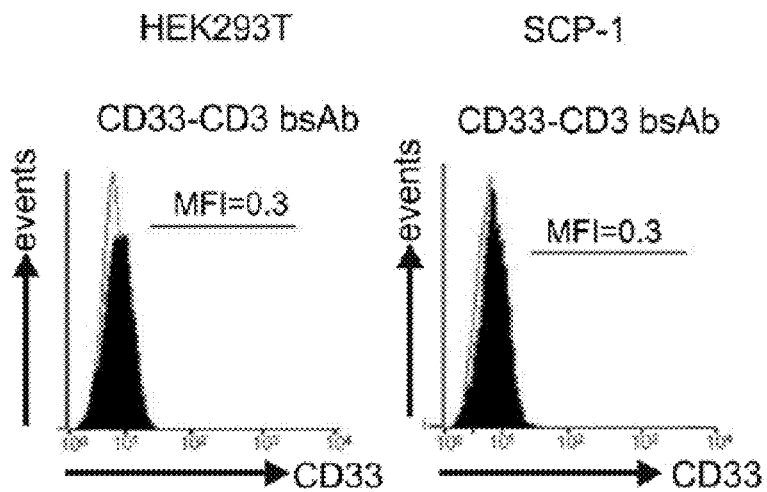
Figure 2C:
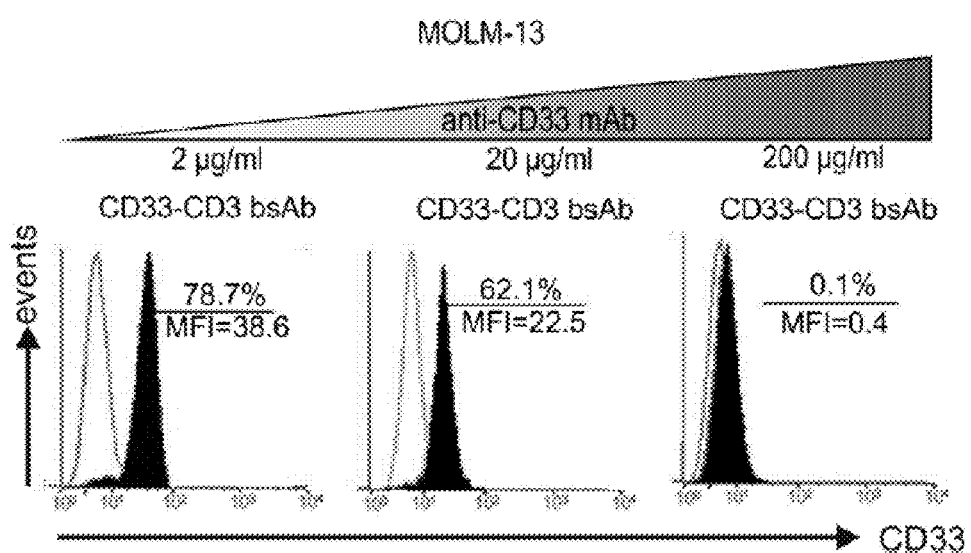

The bsab CD33-CD3 was constructed as a single-chain bispecific tandem fragment variable (scBsTaFv). A schematic representation of the protein structure is given in FIG. 1A. The VH and VL domains of each scFv were humanized by CDR grafting and connected via a linker comprised of three repeats of four glycine and one serine residues 3*(Gly4Ser). The N-terminus of the bsab construct contains a signal peptide (SP) for the secretion of the bsab into the cell culture medium, whereas its C-terminus tag harbors a myc- and his-tag used for immunochemical Ab detection and purification. Binding of the bsab to its target antigens CD3 and CD33 cross-links a T cell and a tumor cell and establishes an immune synapse (FIG. 1B). The parental SCP-1 cell line was examined by flow cytometry at different passages to characterize the surface protein expression. SCP-1 cells expressed the typical MSCs marker proteins CD90, CD105 and CD73 whereas they did not display expression of CD33 antigen or hematopoietic antigens CD45 and CD34. The genetically modified hMSC lines used in this work were generated from the hTERT-immortalized single-cell derived hMSC line SCP-1 [Böcker W, et al. (2008) J Cell Mol Med: 12[4]: 1347-1359] using lentiviral gene transfer to stably express the bsab CD33-CD3. For the identification and selection of successfully transduced cells with bsab gene, the EGFP-zeocin fusion gene was co-expressed under the same promoter through an internal ribosomal entry site (IRES). A lentiviral vector containing only the EGFP-zeocin expression cassette was used for generation of a vector control cell line, whereas untransduced SCP-1 cell line served as 'wild type' (wt) control. Following the SCP-1 cells transduction each hMSC line (wt, vector control and CD33-CD3) was analyzed for intracellular EGFP signal by flow cytometry (FIG. 1C). All cell lines were selected to nearly 100% purity. Next, it was tested if the genetically modified MSCs secrete the bsab. Therefore culture medium was run over affinity chromatography columns to purify bsab CD33-CD3 through the C-terminal his-tag. Indeed, a protein with the expected size of ~60 kDa was detected in the elution fraction by comassie staining (FIG. 1D). Western blotting confirmed the presence of a his-tagged protein at the corresponding molecular size (FIG. 1D). After successful bsab production the amount of bsab CD33-CD3 secreted by the modified MSCs was quantified by ELISA. The maximum bsab concentration obtained from the bsab-releasing hMSCs under these experimental conditions reached 4400 ng/ml at a starting density of $10^5$ hMSC cells/well (FIG. 1E). Considering the sample volume of 200 µl it was calculated that a single MSC releases approximately 8.8 pg bsab in 48 h. However, the highest calculated Ab amount released by a single MSC was obtained at the lowest seeding density ($10^3$ cells/well) reaching 73.7 pg/cell in 48 h. From the antibody release curve it was concluded that the amount of released bsab starts to remain stable above $5\times10^4$ cells/well under the chosen experimental conditions. This observation is most likely due to a rapid nutrient consumption at high seeding densities of hMCSs during the 48 h cultivation period, which in turn down regulates protein synthesis including bsab production in the cells. Next the binding specificity of the purified bsab released by the gene-modified hMSCs was analyzed. In agreement with previous analysis, the binding of both parental monoclonal antibodies lead to a strong shift in MFI (FIG. 2A). The binding capabilities of the MSC-released anti-CD33-anti-CD3 bsab is dependent on surface expression of the respective antigen (FIG. 2A), while no binding can be detected on antigen-negative e.g. HEK293T and SCP-1 cells (FIG. 2B). Furthermore, MSC-released bsab shows a strong binding to the CD33 antigen which can be blocked in a concentration-dependent manner with the parental CD33-specific mab (FIG. 2C). In contrast to the anti-CD33 domain, the binding to the CD3 complex on T cells via the anti-CD3 domain is hardly detectable (FIG. 2A).

Figure 3A:
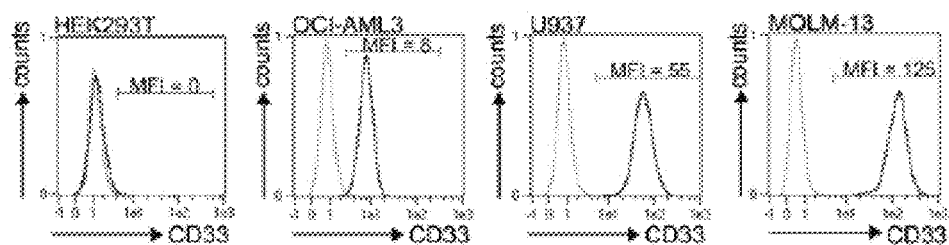
FIGS. 3A-3D: Efficient T cell-mediated killing of target cell lines with varying CD33 expression levels is induced in the presence of bsab-releasing hMSCs.
Figure 3B:
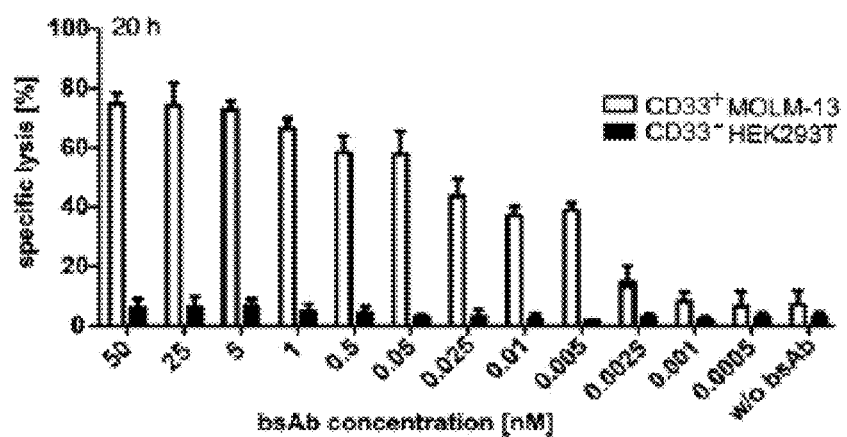
Figure 3C:
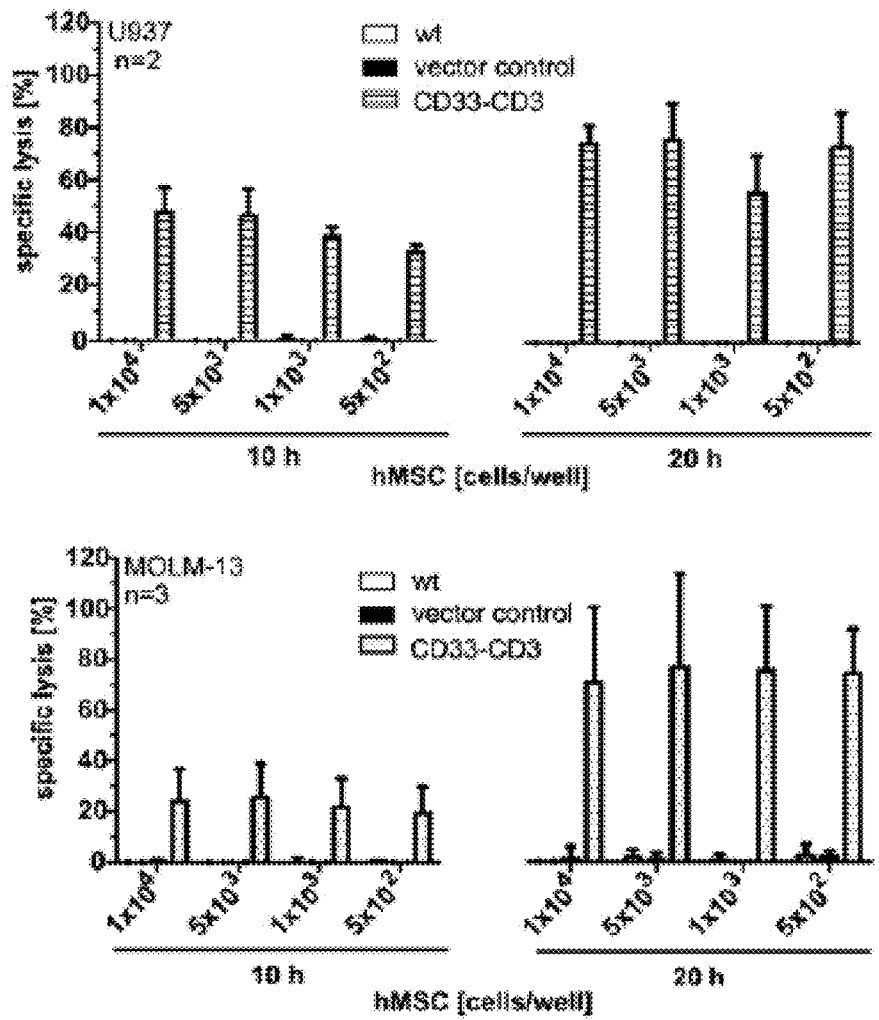
Figure 3D:
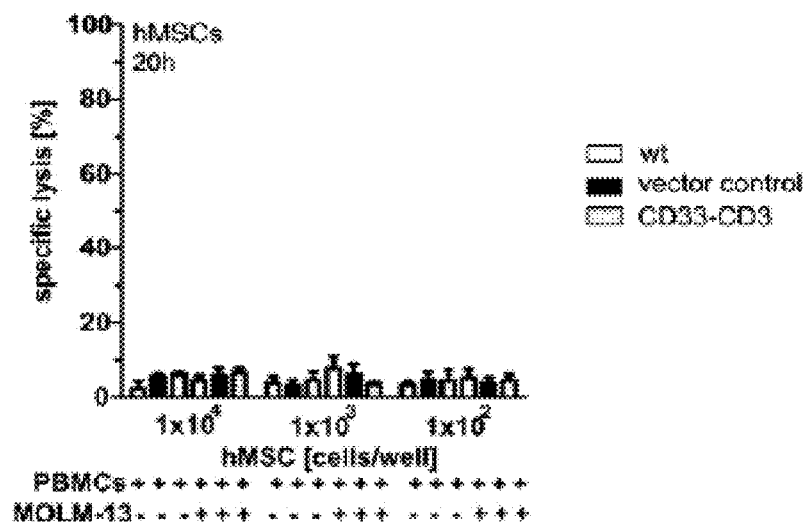

The capability of the MSC-released bsab to redirect T lymphocytes specifically in an antigen-dependent manner was evaluated with various AML cell lines expressing low (OCI-AML3), intermediate (U937) and high (MOLM-13) levels of CD33 antigen (FIG. 3A). HEK293T cells were included in these experiments as a CD33 negative control cell line. Using MOLM-13 cells as targets, it could be demonstrated that human T cells were redirected and mediated target cell killing in a concentration-dependent way in the prescence of the purified anti-CD33-anti-CD3 bsab, whereas CD33 negative HEK293T cells were not attacked by human T cells in the prescence of the bsab (FIG. 3B). Next, retargeting of T lymphocytes to AML cells via in situ bsab-releasing modified hMSCs was evaluated. Therefore, $1\times10^4$ CD3+ T cells were incubated with $^{51}$Cr labeled CD33+ AML cell lines at an e:t cell ratio of 5:1 in the presence of 48 h-cultured hMSC lines. The cross-linkage of T cells and target cells via hMSC-released bsab resulted in effective killing of target cells already at earlier time points independently of the CD33 antigen density on the surface of both analyzed cell lines (FIG. 3C). After prolonged incubation time of 20 h a large portion of target cells were lysed even at low MSC seeding densities (FIG. 3C). No relevant difference in the context of specific target cell lysis between the samples with different hMSC densities was detected, suggesting that T cells can be efficiently redirected against tumor cells even at very low bsab concentrations released by the lowest cell density used in this experimental setting ($5\times10^2$ cells/well). On the contrary no specific lysis was detected in the presence of the wt and vector control hMSC lines, confirming that the observed tumor cell killing was strictly dependent on the bsab release (FIG. 3C). According to the findings herein, the killing efficacy of the hMSC-released bsab CD33-CD3 is within the concentration range of previously published bsab CD33-CD3 data [Stamova S, et al. (2011) Leukemia: 25[6]: 1053-1056; Arndt C, et al. (2013) Leukemia: 27: 964-967; Arndt C, et al. (2014) Leukemia: 28[1]: 59-69]. Moreover, to further exclude any bsab-dependent off-target effect on bsab releasing MSCs, additional killing assays were performed. Therefore, 48 h-cultured $^{51}$Cr labeled gene-modified MSCs were incubated with peripheral blood mononuclear cells to better resemble a natural in vivo situation characterized by the presence of a more complex cell population. No off-target lysis of bsab-expressing hMSCs was observed after 20 h of co-culture of hMSCs and PBMCs in the presence or absence of CD33+ target cells (FIG. 3D), whereas parallel experiments performed under the same conditions showed efficient killing of CD33+ target cells. The obtained results clearly indicate that MSC-secreted bsab is able to redirect human T cells and induce a specific target cell lysis by triggering an efficient T cell activation.

Figure 4A:
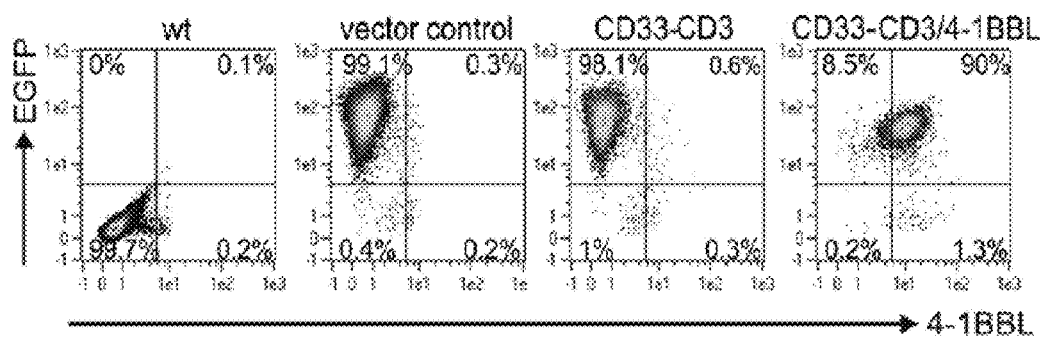
FIGS. 4A-4B: T cell-mediated tumor cell killing elicited by hMSC-produced anti-CD33-anti-bsab is enhanced by co-stimulation from 4-1BBL.
Figure 4B:
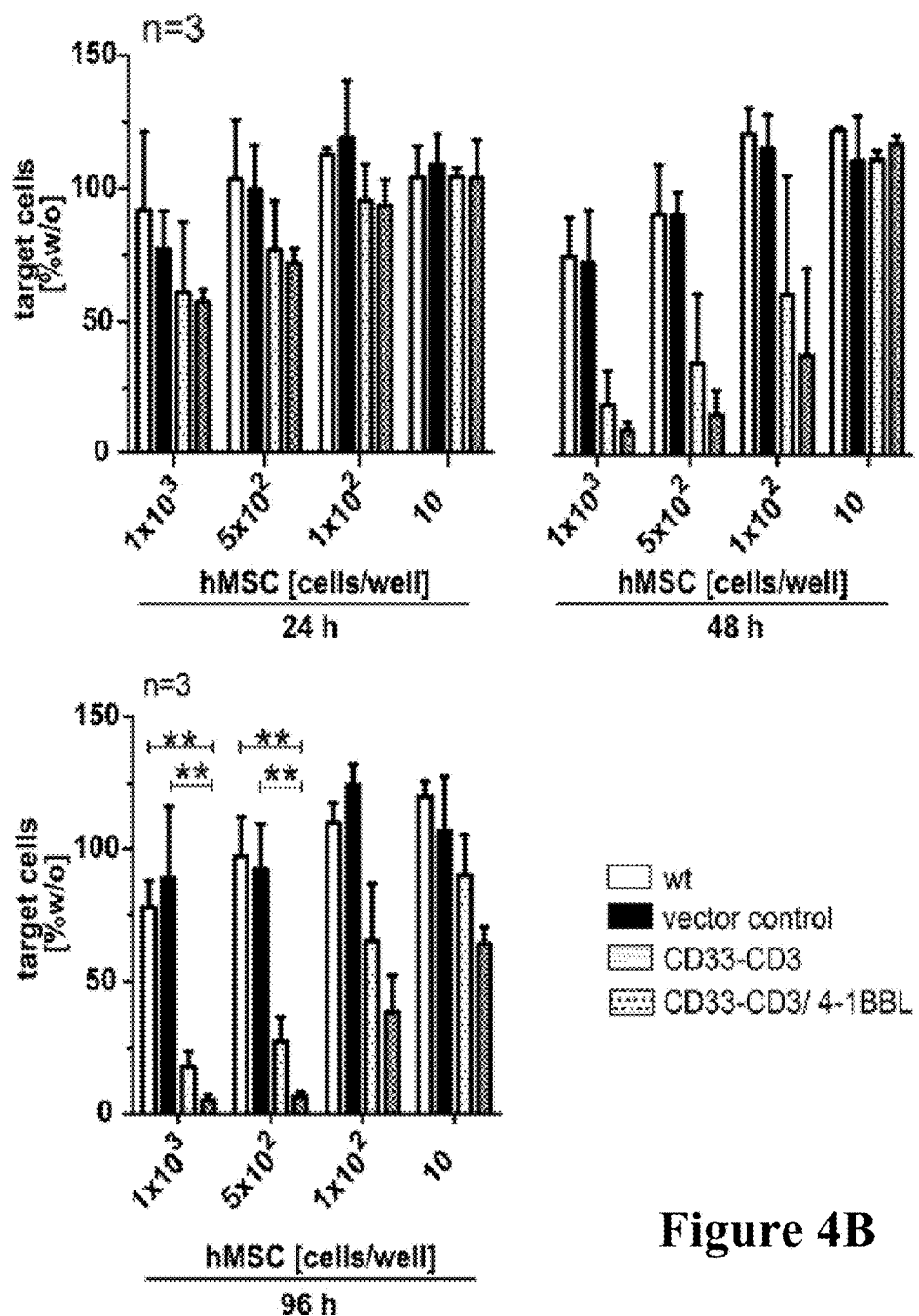

The bsab-releasing hMSCs were further modified by co-expression of the 4-1BBL molecule on the cell surface to prove that the additional co-stimulus led to an enhanced T cell-mediated response even against AML cells expressing low levels of CD33 antigen. Therefore the bsab CD33-CD3 producing hMSC line was additionally genetically modified to express the 4-1BBL molecule. Surface expression of 4-1BBL in the newly generated sub-line could be verified by flow cytometry (FIG. 4A). Next, the immunotherapeutic effect exerted by the modified hMSC sub-lines was investigated by flow cytometry-based cytotoxicity assay. In order to define the lowest hMSCs density leading to a relevant target cell killing effect, hMSCs were seeded at very low concentrations and cultured for 48 h. Subsequently freshly isolated human T cells and EFLUOR®670-labeled CD33low OCI-AML3 target cells were co-incubated together with the modified hMSCs at an e:t ratio of 1:1, which better resembles natural in vivo conditions of AML patients in acute blast crisis having low T cell numbers. The numbers of living target cells were quantified after 24 and 48 h by flow cytometry. T cell mediated target cell lysis triggered by the bsab released from both immunotherapeutic hMSC lines (CD33-CD3 and CD33-CD3+4-1BBL) was delayed and could not be observed before the 48 h time point (FIG. 4B). Co-stimulation by 4-1BBL presented on the surface of the modified hMSC line did not significantly enhance the killing abilities of bsab redirected T cells under these experimental conditions (FIG. 4B).

As it is believed that 4-1BB-mediated co-stimulation is mainly involved in late phases of immune activation and, as such, a longer time may be required to observe a specific T cell response [Arndt C, et al. (2014) Leukemia: 28[1]: 59-69], the co-incubation time period under the same experimental conditions was prolonged. Thus, the percentages of living EFLUOR®670-positive tumor cells were further analyzed after 96 h. After a longer co-incubation time the additional T cell stimulation by hMSC presented 4-1BBL ameliorated the T cell response towards CD33low target cells compared to the hMSCs expressing only the bsab, leading to a more pronounced specific tumor cell killing even at the lowest hMSCs density of 10 MSCs/well (FIG. 4B).

In order to verify the effects of the co-stimulatory signal via 4-1BBL/4-1BB interaction T cell activation, release of pro-inflammatory cytokines and T cell expansion were investigated. In these experiments transgenic CD33+ HEK293T cells, negative for T cell co-stimulatory ligands like B7.1, B7.2, Ox40, 4-1BB and ICOS ligand, were used as target cells instead of CD33+ native AML cell lines to exclude additional T cell stimulation exerted by co-stimulatory molecules.

Figure 5A:
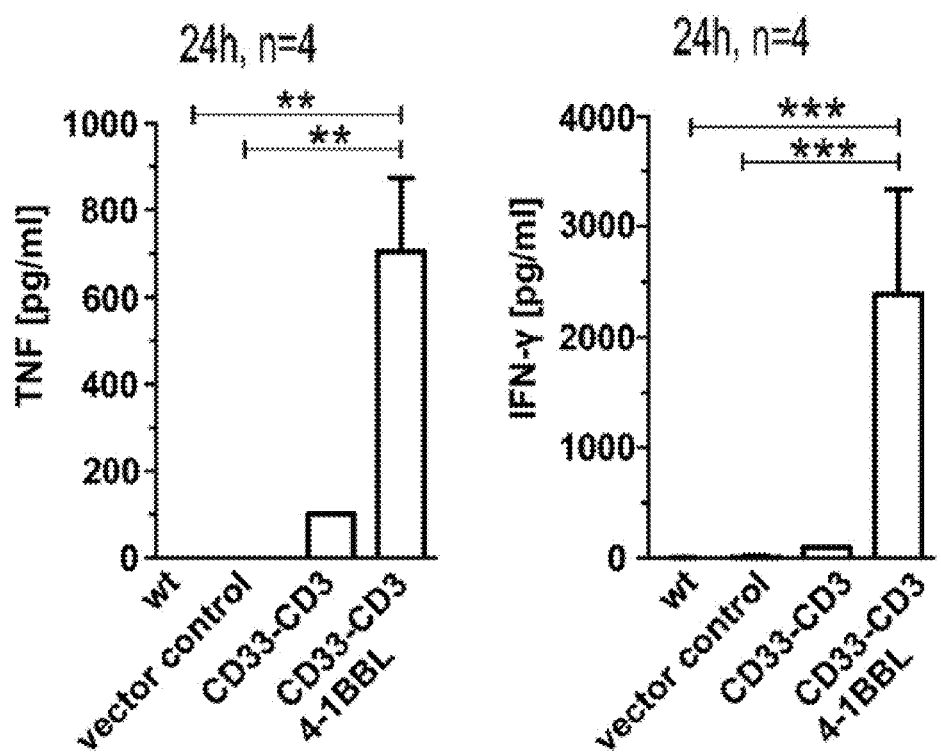
FIGS. 5A-5B: The presence of the co-stimulatory 4-1BBL signal dramatically increases cytokine secretion and T cell expansion.
Figure 5B:
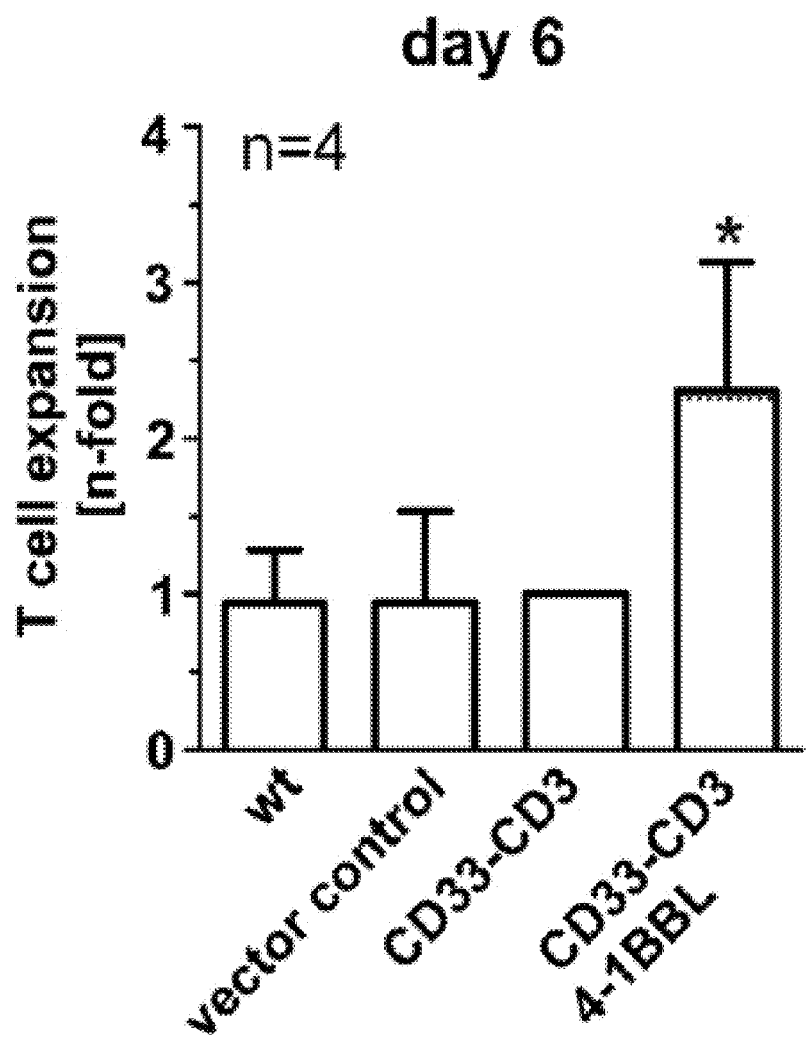

Analyzing the amount of pro-inflammatory cytokines secreted into the supernatants, dramatic differences were detected. Co-stimulation via 4-1BBL expressed on the modified hMSCs increased significantly the levels of IFN-γ and TNF-α secretion up to 8-fold for TNF and more than 10-fold for IFN-γ (FIG. 5A). On the contrary, T cell cross-linkage with CD33+ HEK293T cells without the co-stimulatory signal provoked lower IFN-γ and TNF-α release, while nearly no cytokines were detectable in presence of the wt and vector control hMSCs (FIG. 5A). In accordance to the increased cytokine secretion, cross-linking with immunoligand expressing hMSCs induced stronger proliferation of bsab activated T cells leading to higher expansion rates of T cells in the presence of the 4-1BBL presenting hMSCs (FIG. 5B). T cells expanded approximately two to three fold in the presence of hMSCs expressing the co-stimulatory ligand, whereas no increase in absolute T cells numbers could be observed either in the presence of the CD33-CD3-releasing hMSCs or the parental wt and vector control sub-lines respectively (FIG. 5B).

Figure 6A:
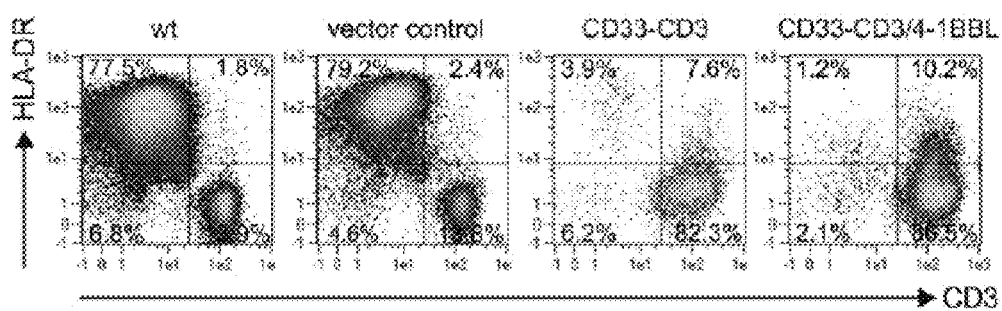
FIGS. 6A-6D: Antitumor effect of redirected AML patient-derived T cells against autologous AML blasts via hMSC-produced bsab CD33-CD3 and surface presented 4-1BBL molecule.
Figure 6B:
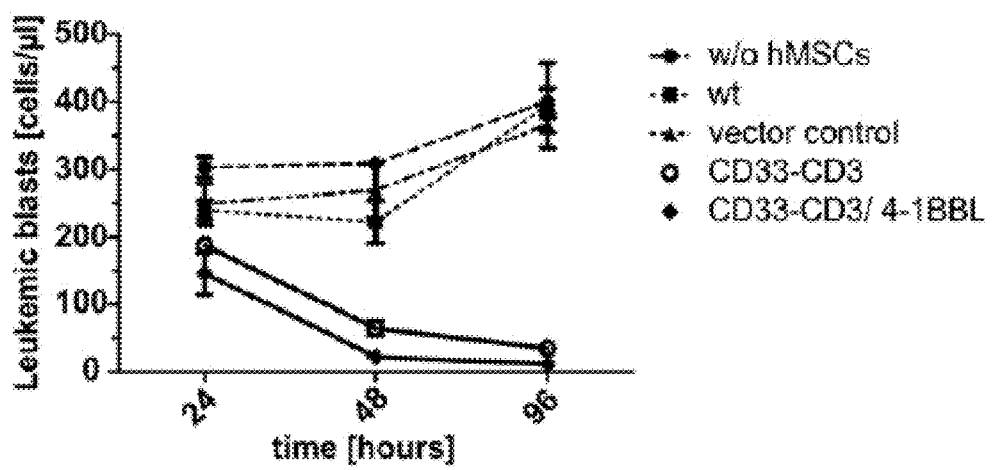

In the next step, CD33-CD3 bsab-producing hMSCs were co-cultivated with AML patient-derived MNCs to investigate their capability to redirect autologous T cells towards AML blasts. Freshly isolated MNCs were phenotyped via immunostaining to measure the proportions of CD45+, CD123+ and HLA-DR+ AML blasts and CD45+, CD3+ T cells respectively. As in previous experimental settings, MSC sub-lines were seeded 48 h beforehand and then co-cultivated with patient-derived MNCs. The relative percentages and the absolute cell numbers of either leukemic cells or leukocyte populations were monitored by flow cytometry upon staining for specific surface markers after 24, 48 and 96 h of co-culture to quantify tumor cell killing and T cell expansion respectively. For one representative donor, already 48 h after starting the co-culture, absolute leukemic blast numbers dramatically decreased, leading to a nearly complete eradication of tumor cells within 96 h (FIG. 6A, FIG. 6B). On the contrary in the presence of the control hMSCs the number of leukemic blasts remained nearly stable over time.

Figure 6C:
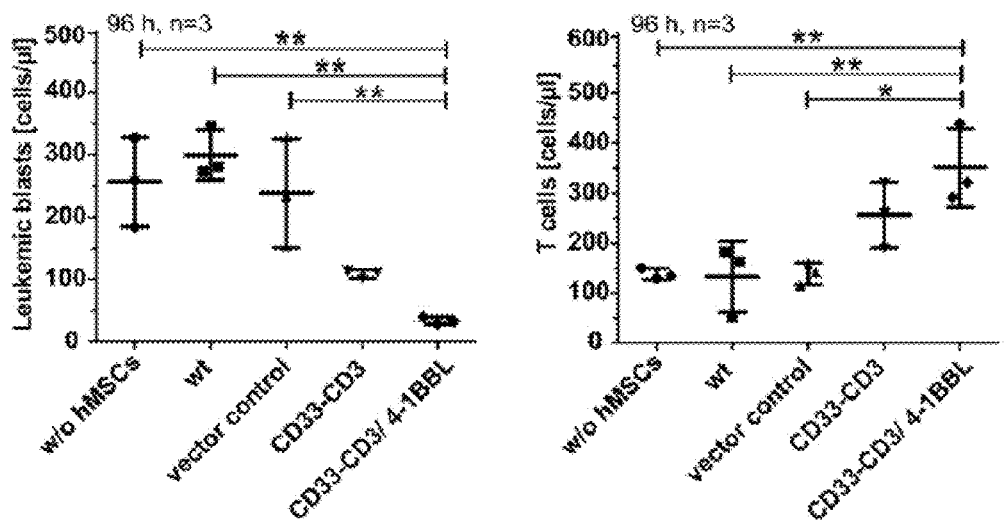
Figure 6D:
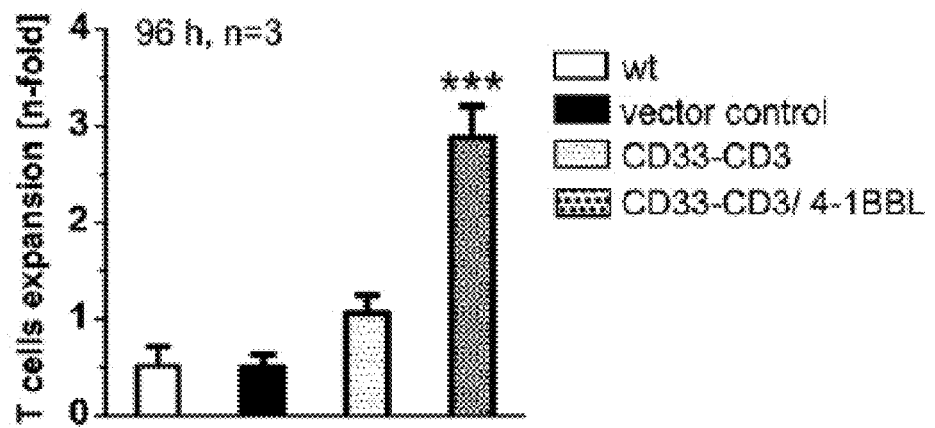

The AML blasts number strongly decreased in the presence of both bsab-releasing hMSCs in comparable manner (FIG. 6A, FIG. 6B, FIG. 6C). handoff note, the presence of the 4-1BB co-stimulatory signal significantly enhanced the proliferation of T cell population after 96 h of co-culture, leading to a doubling of total T cell number and to a pronounced T cell expansion, approximately 3 fold higher compared to the expansion attained in the other samples (FIG. 6C, right panel and FIG. 6D). Altogether, these results show that the continuous delivery of bsab CD33-CD3 together with a constant stimulation of T cells by modified MSCs improve specific killing of autologous AML blasts and increase patient-derived T cells proliferation over time. Moreover, the data show that a co-stimulatory signal for bsab-redirected and -activated T cells need not necessarily be mediated via interaction with the target cells but can also be provided by independent cells.

Figure 7:
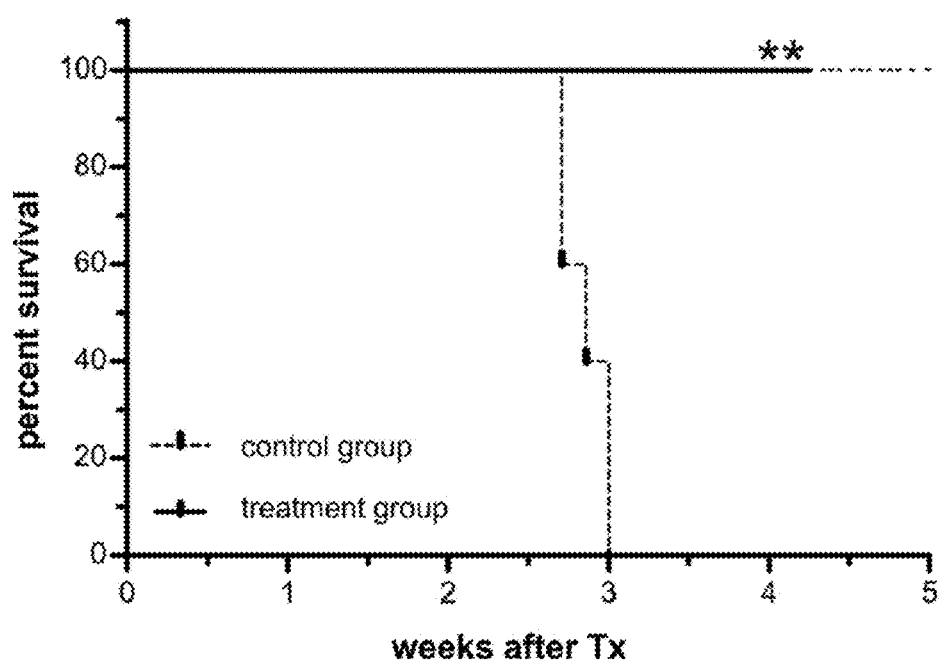
FIG. 7: BsAb-releasing hMSCs prevent the establishment of AML in NOD/SCID IL2Rγ-/- (NSG) mice. (a) Kaplan-Meier survival analysis of NOD/SCID IL2Rγ-/- mice after intravenous injection of T cells and MOLM-13 AML cells at an e:t ratio of 5:1 together with vector control containing (dashed line) or bsab-releasing (black line) hMSCs, indicated as control (n=5) and treatment group (n=4) respectively. A log-rank test was performed to determine the statistical significance in survival between the groups from ongoing experiment. **p<0.01.

The efficacy of the bsab-secreting gene-modified cell system was investigated in vivo by co-injection of 24 h-preincubated MOLM-13 cells, T cells and bsab CD33-CD3 releasing- or vector control containing hMSC lines in NOD/SCID IL2Rγ−/− mice. Daily monitoring of the animals revealed that the mice of the control group injected with vector control-modified hMSCs developed evident signs of leukemic cells engraftment between the second and the third week after transplantation displaying weight loss, reduced locomotion, hunched posture and ruffled fur (FIG. 7). In contrast mice of the treatment group receiving the bsab-releasing hMSCs appeared to be protected from onset of the disease during the experiment. At the time when all untreated control mice had to be killed, all treated mice were still alive and did not show signs of disease (FIG. 7, significance of survival **p<0.01).

Together the data presented herein underline that continuous in situ delivery of bsab CD33-CD3 by genetically modified hMSCs can represent a valid alternative to the exogenous administration of short-lived immunoagents for antigen-specific immunotherapy of AML patients. Moreover, the immunosuppressive potential of MSCs does not limit their use as in vivo bsab factory.

All references (e.g., publications or patents or patent applications) cited herein are incorporated herein by reference in their entirety and for all purposes to the same extent as if each individual reference (e.g., publication or patent or patent application) was specifically and individually indicated to be incorporated by reference in its entirety for all purposes.

Although preferred embodiments have been depicted and described in detail herein, it will be apparent to those skilled in the relevant art that various modifications, additions, substitutions, and the like can be made without departing from the spirit of the invention and these are therefore considered to be within the scope of the invention as defined in the claims which follow.

What is claimed is:

1. An isolated human mesenchymal stem cell (MSC) comprising:
   i) a nucleic acid sequence encoding a bispecific antibody comprising a variable light ($V_L$) antibody domain and variable heavy ($V_H$) antibody domain that specifically bind to CD33 and a $V_L$ antibody domain and $V_H$ antibody domain that specifically bind to CD3, and
   ii) a nucleic acid sequence encoding 4-1BB ligand,
   wherein said MSC expresses and secretes a bispecific antibody capable of specifically binding to CD33 and CD3, and
   wherein said MSC expresses 4-1BB ligand capable of being a human T-cell co-stimulatory ligand.

2. The isolated MSC of claim 1, wherein the nucleic acid sequence encoding the bispecific antibody and the nucleic acid sequence encoding 4-1BB ligand are cDNA.

3. A composition comprising the isolated MSC of claim 1.

4. The composition of claim 3, further comprising a pharmaceutically acceptable carrier.

5. The isolated MSC of claim 1, wherein the $V_L$ antibody domain and $V_H$ antibody domain comprise the amino acid sequences of SEQ ID NO: 3, 4, and 5, and the $V_L$ antibody domain and $V_H$ antibody domain comprise the amino acid sequences of 6, 7, and 8.

* * * * *

SEQUENCE LISTING

<160> NUMBER OF SEQ ID NOS: 32

<210> SEQ ID NO 1
<211> LENGTH: 5
<212> TYPE: PRT
<213> ORGANISM: Artificial Sequence
<220> FEATURE:
<223> OTHER INFORMATION: Chain
<220> FEATURE:
<221> NAME/KEY: CHAIN

```
<222> LOCATION: (1)..(5)

<400> SEQUENCE: 1

Ala Ala Ala Arg Gly
1               5

<210> SEQ ID NO 2
<211> LENGTH: 5
<212> TYPE: PRT
<213> ORGANISM: Artificial Sequence
<220> FEATURE:
<223> OTHER INFORMATION: Chain
<220> FEATURE:
<221> NAME/KEY: Chain
<222> LOCATION: (1)..(5)

<400> SEQUENCE: 2

Ala Ala Gln Pro Ala
1               5

<210> SEQ ID NO 3
<211> LENGTH: 5
<212> TYPE: PRT
<213> ORGANISM: Homo sapiens

<400> SEQUENCE: 3

Asp Tyr Val Val His
1               5

<210> SEQ ID NO 4
<211> LENGTH: 17
<212> TYPE: PRT
<213> ORGANISM: Homo sapiens

<400> SEQUENCE: 4

Tyr Ile Asn Pro Tyr Asn Asp Gly Thr Lys Tyr Asn Glu Lys Phe Lys
1               5                   10                  15

Gly

<210> SEQ ID NO 5
<211> LENGTH: 11
<212> TYPE: PRT
<213> ORGANISM: Homo sapiens

<400> SEQUENCE: 5

Asp Tyr Arg Tyr Glu Val Tyr Gly Met Asp Tyr
1               5                   10

<210> SEQ ID NO 6
<211> LENGTH: 10
<212> TYPE: PRT
<213> ORGANISM: Homo sapiens

<400> SEQUENCE: 6

Thr Ala Ser Ser Ser Val Asn Tyr Ile His
1               5                   10

<210> SEQ ID NO 7
<211> LENGTH: 6
<212> TYPE: PRT
<213> ORGANISM: Homo sapiens

<400> SEQUENCE: 7

Thr Ser Lys Val Ala Ser
1               5
```

<210> SEQ ID NO 8
<211> LENGTH: 9
<212> TYPE: PRT
<213> ORGANISM: Homo sapiens

<400> SEQUENCE: 8

Gln Gln Trp Arg Ser Tyr Pro Leu Thr
1               5

<210> SEQ ID NO 9
<211> LENGTH: 5
<212> TYPE: PRT
<213> ORGANISM: Homo sapiens

<400> SEQUENCE: 9

Ser Tyr Tyr Ile His
1               5

<210> SEQ ID NO 10
<211> LENGTH: 5
<212> TYPE: PRT
<213> ORGANISM: Homo sapiens

<400> SEQUENCE: 10

Asp Tyr Asn Met His
1               5

<210> SEQ ID NO 11
<211> LENGTH: 5
<212> TYPE: PRT
<213> ORGANISM: Homo sapiens

<400> SEQUENCE: 11

Asp Tyr Asn Met Tyr
1               5

<210> SEQ ID NO 12
<211> LENGTH: 5
<212> TYPE: PRT
<213> ORGANISM: Homo sapiens

<400> SEQUENCE: 12

Asp Tyr Val Leu His
1               5

<210> SEQ ID NO 13
<211> LENGTH: 17
<212> TYPE: PRT
<213> ORGANISM: Homo sapiens
<220> FEATURE:
<221> NAME/KEY: misc_feature
<222> LOCATION: (16)..(16)
<223> OTHER INFORMATION: Xaa can be any naturally occurring amino acid

<400> SEQUENCE: 13

Val Ile Tyr Pro Gly Asn Asp Asp Ile Ser Tyr Asn Gln Lys Phe Xaa
1               5                   10                  15

Gly

<210> SEQ ID NO 14
<211> LENGTH: 17
<212> TYPE: PRT
<213> ORGANISM: Homo sapiens

```
<400> SEQUENCE: 14

Tyr Ile Tyr Pro Tyr Asn Gly Gly Thr Gly Tyr Asn Gln Lys Phe Lys
1               5                   10                  15

Ser

<210> SEQ ID NO 15
<211> LENGTH: 17
<212> TYPE: PRT
<213> ORGANISM: Homo sapiens

<400> SEQUENCE: 15

Tyr Ile Asp Pro Tyr Lys Gly Gly Thr Ile Tyr Asn Gln Lys Phe Lys
1               5                   10                  15

Gly

<210> SEQ ID NO 16
<211> LENGTH: 17
<212> TYPE: PRT
<213> ORGANISM: Homo sapiens

<400> SEQUENCE: 16

Leu Ile Asn Thr Tyr Asn Gly Asp Val Arg Tyr Asn Gln Lys Phe Met
1               5                   10                  15

Gly

<210> SEQ ID NO 17
<211> LENGTH: 9
<212> TYPE: PRT
<213> ORGANISM: Homo sapiens

<400> SEQUENCE: 17

Glu Val Arg Leu Arg Tyr Phe Asp Val
1               5

<210> SEQ ID NO 18
<211> LENGTH: 7
<212> TYPE: PRT
<213> ORGANISM: Homo sapiens

<400> SEQUENCE: 18

Gly Arg Pro Ala Met Asp Tyr
1               5

<210> SEQ ID NO 19
<211> LENGTH: 10
<212> TYPE: PRT
<213> ORGANISM: Homo sapiens

<400> SEQUENCE: 19

Gln Met Ile Thr Ala Tyr Tyr Phe Asp Tyr
1               5                   10

<210> SEQ ID NO 20
<211> LENGTH: 11
<212> TYPE: PRT
<213> ORGANISM: Homo sapiens

<400> SEQUENCE: 20

Asp Tyr Arg Tyr Glu Tyr Tyr Ala Met Asp Tyr
1               5                   10

<210> SEQ ID NO 21
```

```
<211> LENGTH: 17
<212> TYPE: PRT
<213> ORGANISM: Homo sapiens

<400> SEQUENCE: 21

Lys Ser Ser Gln Ser Val Phe Phe Ser Ser Gln Lys Asn Tyr Leu
1               5                   10                  15

Ala

<210> SEQ ID NO 22
<211> LENGTH: 15
<212> TYPE: PRT
<213> ORGANISM: Homo sapiens

<400> SEQUENCE: 22

Arg Ala Ser Glu Ser Val Asp Asn Tyr Gly Ile Ser Phe Met Asn
1               5                   10                  15

<210> SEQ ID NO 23
<211> LENGTH: 11
<212> TYPE: PRT
<213> ORGANISM: Homo sapiens

<400> SEQUENCE: 23

Lys Ala Ser Gln Asp Ile Asn Lys Tyr Ile Ala
1               5                   10

<210> SEQ ID NO 24
<211> LENGTH: 10
<212> TYPE: PRT
<213> ORGANISM: Homo sapiens

<400> SEQUENCE: 24

Ser Ala Asn Ser Ser Val Ser Tyr Ile His
1               5                   10

<210> SEQ ID NO 25
<211> LENGTH: 7
<212> TYPE: PRT
<213> ORGANISM: Homo sapiens

<400> SEQUENCE: 25

Trp Ala Ser Thr Arg Glu Ser
1               5

<210> SEQ ID NO 26
<211> LENGTH: 6
<212> TYPE: PRT
<213> ORGANISM: Homo sapiens

<400> SEQUENCE: 26

Ala Ser Asn Gln Gly Ser
1               5

<210> SEQ ID NO 27
<211> LENGTH: 6
<212> TYPE: PRT
<213> ORGANISM: Homo sapiens

<400> SEQUENCE: 27

Thr Ser Thr Leu Gln Pro
1               5

<210> SEQ ID NO 28
```

```
<211> LENGTH: 6
<212> TYPE: PRT
<213> ORGANISM: Homo sapiens

<400> SEQUENCE: 28

Thr Ser Lys Leu Ala Ser
1               5

<210> SEQ ID NO 29
<211> LENGTH: 8
<212> TYPE: PRT
<213> ORGANISM: Homo sapiens

<400> SEQUENCE: 29

His Gln Tyr Leu Ser Ser Arg Thr
1               5

<210> SEQ ID NO 30
<211> LENGTH: 9
<212> TYPE: PRT
<213> ORGANISM: Homo sapiens

<400> SEQUENCE: 30

Gln Gln Ser Lys Glu Val Pro Trp Thr
1               5

<210> SEQ ID NO 31
<211> LENGTH: 8
<212> TYPE: PRT
<213> ORGANISM: Homo sapiens

<400> SEQUENCE: 31

Leu Gln Tyr Asp Asn Leu Leu Thr
1               5

<210> SEQ ID NO 32
<211> LENGTH: 9
<212> TYPE: PRT
<213> ORGANISM: Homo sapiens

<400> SEQUENCE: 32

Gln Gln Trp Thr Ser His Pro Leu Thr
1               5
```